United States Patent [19]
Hewawasam et al.

[11] Patent Number: 5,972,961
[45] Date of Patent: Oct. 26, 1999

[54] 4-ARYL-3-AMINOQUINOLINE-2-ONE DERIVATIVES AS POTASSIUM CHANNEL MODULATORS

[75] Inventors: Piyasena Hewawasam; John E. Starrett, Jr., both of Middletown, Conn.; Stephen G. Swartz, Warrington, Pa.

[73] Assignee: Bristol-Myers Squibb Company, Princeton, N.J.

[21] Appl. No.: 09/138,638

[22] Filed: Aug. 24, 1998

Related U.S. Application Data

[60] Provisional application No. 60/058,014, Aug. 28, 1997.

[51] Int. Cl.$^6$ .......................... C07D 215/16; A01N 43/42
[52] U.S. Cl. ........................... 514/312; 514/313; 546/157
[58] Field of Search ............................ 546/157; 514/312, 514/313

[56] References Cited

U.S. PATENT DOCUMENTS

| | | | |
|---|---|---|---|
| 3,202,661 | 8/1965 | Brust et al. ............................... | 546/157 |
| 5,200,422 | 4/1993 | Olesen et al. ............................ | 514/387 |
| 5,565,472 | 10/1996 | Hamanaka ................................ | 514/312 |
| 5,565,483 | 10/1996 | Hewawasam et al. ................... | 514/411 |

FOREIGN PATENT DOCUMENTS

| | | |
|---|---|---|
| 477819 | 4/1992 | European Pat. Off. . |
| WO 93/08800 | 5/1993 | WIPO . |

OTHER PUBLICATIONS

Ahmed, F. et al., "Some Features of the Spasmogenic Actions of Acetylcholine and Histamine in Guinea–Pig Isolated Trachealis", *Br. J. Pharmacol.*, 83, pp. 227–233 (1984).

Baró, I. and Escande, D., "A $Ca^{2+}$–activated $K^+$ Current in Guinea–pig Atrial Myocytes", *Pflügers Archiv.*, 414(Suppl. 1), pp. S168–S–170 (1989).

Cook, N.S., "The Pharmacology of Potassium Channels and Their Therapeutic Potential", *Trends in Pharmacol. Sciences*, 9, pp. 21–28 (Jan., 1988).

Koh, D–S., et al., "Effect of the Flavoid Phloretin on $Ca^{2+}$–activated $K^+$ Channels in Myelinated Nerve Fibres of *Xenopus Laevis*", *Neuroscience Lett.* 165, pp. 167–170 (1994).

Laurent, F. et al., "Evaluation of the Relaxant Effects of SCA40, A Novel Charybdotoxin–Sensitive Potassium Channel Opener, in Guinea–Pig Trachealis", *Br. J. Pharmacol.*, 108, pp. 622–626 (1993).

Masoud, M. S., et al, "Spectral Studies on Some 2–Quinolones", *Spectroscopy Letters*, 21(6), pp. 369–383 (1988).

Masoud, M. S., et al., "Solution Equilibria and Structures of Some 2–Quinolone Iron (III), Cobalt (II), Nickel (II) and Copper (II) Complexes", *Synth. React. Inorg. Met.–Org. Chem.*, 17, (8 & 9), pp. 881–899 (1987).

*The Merck Index*, 11th Edition, p. 1575 (1989).

Mohammed, Y. S., et al, "Synthesis of 4–Substituted–3–hydroxy–2–quinolones and Azines", *Pharmazie*, 40, pp. 312–314 (1985).

Olesen, S.–P., et al, "Selective Activation of $Ca^{2+}$–dependent $K^+$channels by Novel Benzimidazolone", *European J. Pharmacol.*, 251, pp. 53–59 (1994).

Quast, U. and Cook, N. S, "Moving Together: $K^+$ Channel Openers and ATP–sensitive $K^+$Channels", *Trends in Pharmacol. Sciences*, 10, pp. 431–435 (Nov., 1989).

Singer, J. J. and Walsh, J.V., "Characterization of Calcium–activated Potassium Channels in Single Smooth Muscle Cells Using the Patch–clamp Technique", *Pflügers Archiv.*, 408, pp. 98–111 (1987).

Trivedi, S., et al., "Calcium Dependent K–Channels In Guinea Pig and Human Urinary Bladder", *Biochemical and Biophysical Research Communications*, 213, No. 2, pp. 404–409 (Aug., 1995).

Walser, A., et al, "Cyclization Products Derived from o–Benzoyl Malonanilates", *J. Org. Chem.*, 38, (3), pp. 449–456 (1973).

Primary Examiner—D M Mach
Attorney, Agent, or Firm—Aldo A. Algieri

[57] ABSTRACT

The present invention provides novel 4-aryl-3-aminoquinolin-2-one derivatives having the general formula

I

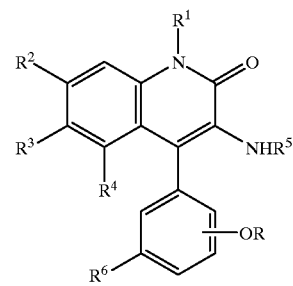

wherein R, $R^1$, $R^2$, $R^3$, $R^4$, $R^5$ and $R^6$ are as defined herein, or a non-toxic pharmaceutically acceptable salt thereof which are modulators of the large conductance calcium-activated $K^+$ channels and are useful in the treatment of disorders which are responsive to the opening of the potassium channels.

9 Claims, No Drawings

4-ARYL-3-AMINOQUINOLINE-2-ONE DERIVATIVES AS POTASSIUM CHANNEL MODULATORS

CROSS REFERENCE TO RELATED APPLICATION

This nonprovisional application claims the benefit of provisional application, U.S. Ser. No. 60/058,014, filed Aug. 28, 1997, now abandoned.

FIELD OF THE INVENTION

The present invention is directed to novel 4-aryl-3-aminoquinolin-2-one derivatives which are modulators of the large-conductance calcium-activated potassium (BK) channels and, therefore, useful in the protection of neuronal cells and diseases arising from dysfunction of cellular membrane polarization and conductance. The present invention also provides a method of treatment with the novel substituted quinolin-2-one derivatives and to pharmaceutical compositions thereof.

BACKGROUND OF THE INVENTION

Potassium channels play a key role in regulation of cell membrane potential and modulation of cell excitability. Potassium channels are largely regulated by voltage, cell metabolism, calcium and receptor mediated processes. [Cook, N. S., *Trends in Pharmacol. Sciences* (1988), 9, 21; and Quast, U., et al, *Trends in Pharmacol. Sciences* (1989), 10, 431]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance<50 pS. Large-conductance calcium-activated potassium (Maxi-K or BK) channels are present in many excitable cells including neurons, cardiac cells and various types of smooth muscle cells. [Singer, J. et al., *Pflugers Archiv.* (1987) 408, 98; Baro, I., et al., *Pflugers Archiv.* (1989) 414 (Suppl. 1), S168; and Ahmed, F. et al., *Br. J. Pharmacol.* (1984) 83, 227].

Potassium ions play a dominant role in controlling the resting membrane potential in most excitable cells and maintain the transmembrane voltage near the $K^+$ equilibrium potential ($E_k$) of about −90 mV. It has been shown that opening of potassium channels shift the cell membrane potential towards the equilibrium potassium membrane potential ($E_k$), resulting in hyperpolarization of the cell. [Cook, N. S., *Trends in Pharmacol. Sciences* (1988), 9, 21]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells.

A range of synthetic and naturally occurring compounds with BK opening activity have been reported. The avena pyrone extracted from avena sativa-common oats has been identified as a BK channel opener using lipid bi-layer technique [International Patent application WO 93/08800, published May 13, 1993]. 6-Bromo-8-(methylamino) imidazo[1,2-a]pyrazine-2-carbonitrile (SCA-40) has been described as a BK channel opener with very limited electrophysiological experiments [Laurent, F. et al., *Br. J. Pharmacol.* (1993) 108, 622–626]. The flavanoid, Phloretin has been found to increase the open probability of $Ca^{2+}$-activated potassium channels in myelinated nerve fibers of *Xenopus laevis* using outside-out patches [Koh, D-S., et al., *Neuroscience Lett.* (1994) 165, 167–170].

In European patent application EP-477,819 published Jan. 4, 1992 and corresponding U.S. Pat. No. 5,200,422, issued Apr. 6,1993 to Olesen, et al., a number of benzimidazole derivatives were disclosed as openers of BK channels by using single-channel and whole-cell patch-clamp experiments in aortic smooth muscle cells. Further work was reported by Olesen, et al in *European J. Pharmacol.*, 251, 53–59 (1994).

A number of substituted oxindoles have been disclosed as openers of BK channels by P. Hewawasam, et al, in U.S. Pat. No. 5,565,483, issued Oct. 15, 1996.

E. S. Hamanaka in U.S. Pat. No. 5,565,472, issued Oct. 15, 1996, discloses a number of 4-aryl-3-(heteroarylureido)-1,2-dihydro-2-oxo-quinoline derivatives which are inhibitors of acyl coenzyme A; cholesterol acyltransferase and are useful as hypolipidemic and antiatherosclerosis agents.

A. Walser, et al, *J. Org. Chem.*, 38, 449–456 (1973) disclose a limited number of 3-hydroxyquinolinones as by-products formed during the opening of the epoxide intermediate.

Y. S. Mohammed, et al, *Pharmazie*, 40, 312–314 (1985) discloses a series of 4-substituted-3-hydroxy-2-quinolones as analogues of the natural product viridicatin. *The Merck Index*, 11th Edition, 1575 (1989) briefly summarizes the references to the antibiotic substance, viridicatin.

M. S. Masoud, et al, in *Spectroscopy Letters*, 21 (6), 369–383 (1988) describe the spectral properties of several 2-quinolones as liquids and in *Synth. React. Inorg. Met.-Org. Chem.*, 17, (8 & 9), 881–899 (1987) describe the equilibria and stability of the 2-quinolones in metallic complexes.

It is the object of the present invention to provide novel compounds that will modulate potassium channels, in particular, large-conductance calcium-activated potassium (BK) channels which will be useful in reducing neuronal damage.

SUMMARY OF THE INVENTION

The present invention provides novel 4-aryl-3-aminoquinolin-2-one derivatives having the general formula

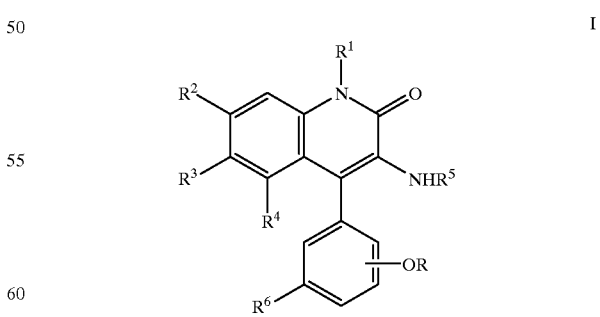

I wherein R, $R^1$, $R^2$, $R^3$, $R^4$, $R^5$ and $R^6$ are as defined below, or a non-toxic pharmaceutically acceptable salt thereof which are openers of the large conductance calcium-activated $K^+$ channels also known as Maxi-K or BK channels. The present invention also provides pharmaceutical compositions comprising said quinolin-2-one derivatives and to the method of treatment of disorders sensitive to potassium channel opening activity such as ischemia, stroke, convulsions, epilepsy, asthma, irritable bowel syndrome, migraine, traumatic brain injury, spinal cord injury, male erectile dysfunction and urinary incontinence.

DETAILED DESCRIPTION OF THE INVENTION

The present invention provides novel 4-aryl-3-aminoquinolin-2-one derivatives which are potent openers of the high conductance, calcium-activated $K^+$-channels (BK channel) and which have the formula

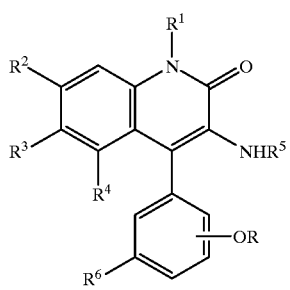

I wherein

R and $R^1$ each are independently hydrogen or methyl; $R^2$, $R^3$ and $R^4$ each are independently hydrogen, halogen, nitro or trifluoromethyl;

$R^5$ is hydrogen, $C_{1-4}$alkyl, $C_{1-4}$alkylsulfonyl, trifluoromethylsulfonyl, naphthylsulfonyl, $C_{1-4}$alkylcarbonyl, diphenylphosphinyl, cyclohexylmethyl, pyridylmethyl, furanylmethyl, furanyl-2-propenyl, imidazolylmethyl, thienylmethyl, 1-methyl pyrrolylmethyl, unsubstituted or substituted phenyl, phenylmethyl, phenylsulfonyl, phenylcarbonyl, phenylalkylcarbonyl or phenylglyoxyloyl, wherein said phenyl substituent is selected from the group consisting of one or two fluoro, hydroxy, trifluoromethyl, amino, methoxy, methylthio and nitro; and $R^6$ hydrogen, bromo, chloro or nitro; or a nontoxic pharmaceutically acceptable salt thereof.

The present invention also provides a method for the treatment or alleviation of disorders associated with BK channels, especially ischemia, stroke, convulsions, epilepsy, asthma, irritable bowel syndrome, migraine, traumatic brain injury, spinal cord injury, male erectile dysfunction and urinary incontinence which comprises administering together with a conventional adjuvant, carrier or diluent a therapeutically effective amount of a compound of formula I or a nontoxic pharmaceutically acceptable salt thereof.

The term "nontoxic pharmaceutically acceptable salt" as used herein and in the claims is intended to include nontoxic base addition salts with inorganic bases. Suitable inorganic bases such as alkali and alkaline earth metal bases include metallic cations such as sodium, potassium, magnesium, calcium and the like.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the method that is sufficient to show a meaningful patient benefit, i.e., healing of acute conditions characterized by openers of large conductance calcium-activated $K^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

Preferred compounds for use in the method of this invention include the compounds of Formula I listed below:

3-Amino-4-(5-chloro-2-hydroxyphenyl)-6-(trifluoromethyl) quinolin-2(1H)-one;

3-Amino-4-(5-chloro-2-hydroxyphenyl)-7-(trifluoromethyl) quinolin-2(1H)-one;

4-(5-Chloro-2-hydroxyphenyl)-3-(methylamino)-6-(trifluoromethyl) quinolin-2(1H)-one;

N-[4-(5-Chloro-2-hydroxyphenyl)-2-oxo-6-(trifluoromethyl)-1H-quinolin-3-yl] trifluoromethanesulfonamide;

N-[4-(5-Chloro-2-hydroxyphenyl)-2-oxo-7-(trifluoromethyl)-1H-quinolin-3-yl] trifluoromethanesulfonamide;

N-[4-(5-Chloro-2-hydroxyphenyl)-2-oxo-6-(trifluoromethyl)-1H-quinolin-3-yl]methanesulfonamide;

N-[4-(5-Chloro-2-hydroxyphenyl)-2-oxo-6-(trifluoromethyl)-1H-quinolin-3-yl]phenylsulfonamide;

3-Amino-4-(5-chloro-2-hydroxyphenyl)-5,7-dichloroquinolin-2(1H)-one;

N-[4-(5-Chloro-2-hydroxyphenyl)-2-oxo-6-(trifluoromethyl)-1H-quinolin-3-yl]aminocarboxylic acid, phenylmethyl ester;

3-Amino-4-(5-chloro-2-hydroxyphenyl)-6-nitroquinolin-2 (1H)-one;

3-Amino-4-(5-chloro-2-hydroxyphenyl)-7-nitroquinolin-2 (1H)-one;

N-[4-(5-Chloro-2-hydroxyphenyl)-2-oxo-6-(trifluoromethyl)-1H-quinolin-3-yl] diphenylphosphinamid;

3-Amino-4-(5-chloro-2-hydroxyphenyl)-5,6-dichloroquinolin-2(1H)-one;

N-[4-(5-Chloro-2-hydroxyphenyl)-2-oxo-6-(trifluoromethyl)-1H-quinolin-3-yl]-4-hydroxybenzenesulfonamide;

3-Amino-4-(5-chloro-2-hydroxyphenyl)-5-(trifluoromethyl) quinolin-2(1H)-one;

3-Amino-4-(5-chloro-2-hydroxyphenyl)-5,7-bis (trifluoromethyl)quinolin-2(1H)-one;

3-Amino-4-(5-chloro-2-hydroxyphenyl)-6-chloroquinolin-2 (1H)-one;

3-Amino-4-(5-chloro-2-hydroxyphenyl)-6-chloro-7-(trifluoromethyl) quinolin-2(1H)-one;

3-Amino-4-(5-chloro-2-hydroxyphenyl)-6-chloro-5-(trifluoromethyl) quinolin-2(1H)-one;

3-Amino-4-(5-chloro-2-hydroxyphenyl)-6-iodoquinolin-2 (1H)-one;

4-(5-Chloro-2-hydroxyphenyl)-3-[(4-hydroxyphenyl)amino]-6-(trifluoromethyl)quinolin-2(1H)-one;

4-(5-Chloro-2-hydroxyphenyl)-3-[(3,5-dihydroxyphenyl)-amino]-6-(trifluoromethyl)quinolin-2(1H)-one;

4-(5-Chloro-2-methoxyphenyl)-3-[(3,5-dihydroxyphenyl)-amino]-6-(trifluoromethyl)quinolin-2(1H)-one;

4-(5-Chloro-2-methoxyphenyl)-3-[(4-hydroxyphenyl)amino]-6-(trifluoromethyl)quinolin-2(1H)-one;

N-[4-(5-Chloro-2-hydroxyphenyl)-2-oxo-6-(trifluoromethyl)-1H-quinolin-3-yl]-4-(trifluoromethyl)benzenesulfonamide;

N-[4-(5-Chloro-2-hydroxyphenyl)-1-methyl-2-oxo-6-(trifluoro-methyl)-1H-quinolin-3-yl]-4-nitrobenzenesulfonamide;

3-Amino-4-(4-hydroxyphenyl)-6-(trifluoromethyl)quinolin-2(1H)-one;

3-Amino-4-(5-bromo-2-hydroxy-phenyl)-6-(trifluoromethyl)quinolin-2(1H)-one;

N-[4-(5-Chloro-2-hydroxyphenyl)-2-oxo-6-(trifluoromethyl)-1H-quinolin-3-yl]-4-nitrobenzenesulfonamide;

N-[4-(5-Chloro-2-hydroxyphenyl)-2-oxo-6-(trifluoromethyl)-1H-quinolin-3-yl]-(4-fluorobenzene)sulfonamide;

3-Amino-4-(5-chloro-2-hydroxy-phenyl)-1-methyl-6-(trifluoro-methyl) quinolin-2(1H)-one;

3-Amino-4-(2-hydroxy-5-nitro-phenyl)-6-(trifluoromethyl)quinolin-2(1H)-one;

3-Amino-4-(3-chloro-4-hydroxy-phenyl)-6-(trifluoromethyl)quinolin-2(1H)-one 4-(5-Chloro-2-methoxyphenyl)-3-(methylamino)-6-(trifluoromethyl)quinolin-2(1H)-one;

4-(5-Chloro-2-methoxyphenyl)-3-[(4-pyridylmethyl)amino]-6-(trifluoromethyl)quinolin-2(1H)-one;

4-(5-Chloro-2-methoxyphenyl)-3-[(phenylmethyl)amino]-6-(trifluoromethyl)quinolin-2(1H)-one;

4-(5-Chloro-2-methoxyphenyl)-3-[(2-furanylmethyl)amino]-6-(trifluoromethyl)quinolin-2(1H)-one;

(5-Chloro-2-methoxyphenyl)-3-[(2-imidazolylmethyl)amino]-6-(trifluoromethyl)quinolin-2(1H)-one;

4-(5-Chloro-2-methoxyphenyl)-3-[(3-thienylmethyl)amino]-6-(trifluoromethyl)quinolin-2(1H)-one;

4-(5-Chloro-2-methoxyphenyl)-3-[(1-methyl pyrrolylmethyl)amino]-6(trifluoromethyl)quinolin-2(1H)-one;

4-(5-Chloro-2-methoxyphenyl)-3-[[(4-fluoro phenyl)methyl]amino]-6-(trifluoromethyl)quinolin-2(1H)-one;

4-(5-Chloro-2-methoxyphenyl)-3-[(3-pyridylmethyl)amino]-6-(trifluoromethyl)quinolin-2(1H)-one;

4-(5-Chloro-2-methoxyphenyl)-3-[(2-furanylmethyl)amino]-6-(trifluoromethyl)quinolin-2(1H)-one;

4-(5-Chloro-2-methoxyphenyl)-3-[[(2-furanyl)-2-propenyl]amino]-6-(trifluoromethyl)quinolin-2(1H)-one;

4-(5-Chloro-2-methoxyphenyl)-3-[[[4-(thiomethyl)phenyl]-methyl]amino]-6-(trifluoromethyl)quinolin-2(1H)-one;

4-(5-Chloro-2-methoxyphenyl)-3-[(cyclohexylmethyl)amino]-6-(trifluoromethyl)quinolin-2(1H)-one; and 4-(5-Chloro-2-methoxyphenyl)-3-[[[4-(methoxy)phenyl]methyl]amino]-6-(trifluoromethyl)quinolin-2(1H)-one.

The compounds of Formula I may be prepared by various procedures such as those illustrated herein in the the examples, in the Reaction Schemes and variations thereof which would be evident to those skilled in the art.

3-Aminoguinolin-2(1H)-ones

3-Aminoquinolin-2(1H)-one derivatives were prepared as outlined in Reaction Schemes 1 and 2. The starting 2-aminobenzophenones precursors were prepared by a variety of methods as depicted in Reaction Scheme 1. Reaction Scheme 2 represents the general route used for conversion of 2-aminobenzophenones to 3-aminoquinolin-2(1H)-ones. Further functionalization of the 3-amino moiety of the 3-aminoquinolin-2(1H)-ones were carried out as outlined in Reaction Schemes 3, 4 and 5. The N-benzylation of the 3-amino moiety was carried out as depicted in Scheme 6 while N-alkylation of the 3-amino moiety was carried out by the general reaction depicted in Scheme 9. N-Aryl-3-aminoquinolinones were prepared as outlined in Reaction Schemes 6, 7 and 8.

Reaction Scheme 1

Scheme 1.1

Method A: Directed Lithiation of Protected Anilines

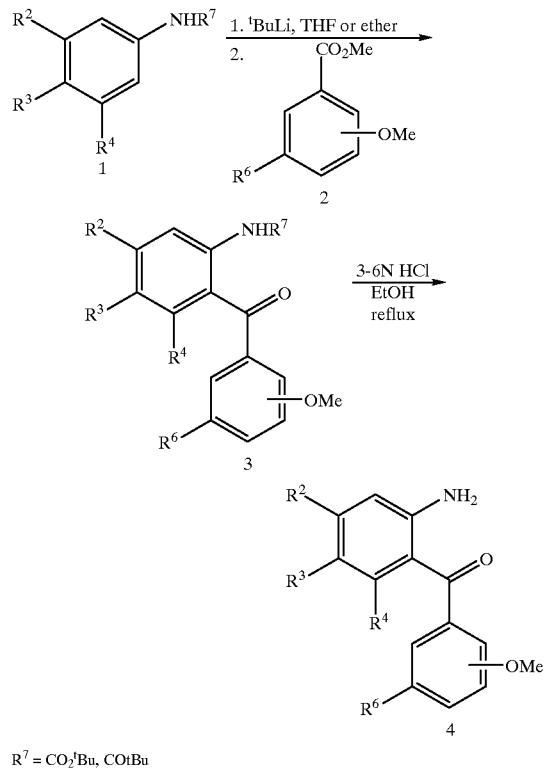

$R^7 = CO_2{}^tBu, COtBu$

Directed lithiation of a variety of protected anilines were employed for the preparation of requisite 2-aminobenzophenone precursors (4). The protocol utilizes the reaction of an ortholithiated, protected aniline derivative (1) with an aryl ester (2) to furnish a benzophenone derivative (3). It is well established that when the amino group of an aniline is suitably protected it can direct metalation to the ortho position. Thus, N-Boc- and N-pivaloylanilines were widely used to prepare ortho-substituted aniline derivatives via the corresponding dianion species. The pattern of substitution of the 2-aminobenzophenones produced by this method is dependent upon the regiospecificity of the directed metalation.

Scheme 1.2

Method B: Addition of aryl Grignard reagents to benzoxazinones

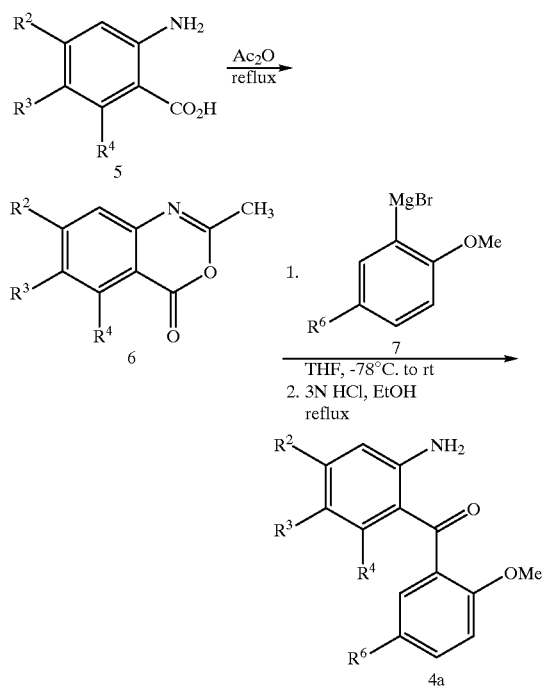

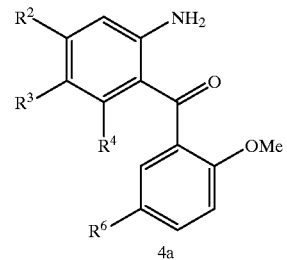

The benzoxazinones (6) were generated by reaction of anthranilic acids (5) with excess acetic anhydride at reflux. Addition of (5-chloro-2-methoxyphenyl)magnesium bromide $R^6$=Cl to a THF solution of the benzoxazinone 6 provided the desired N-acetyl-2-aminobenzophenone derivatives. In general, when the substituents on the benzoxazinone nucleus are non-reactive towards the aryl Grignard reagent, N-acetyl-2-aminobenzophenones can be prepared in quite good yield. Deacetylation with 3N HCl in refluxing ethanol provided the desired 2-aminobenzophenones (4a).

Scheme 1.3

Method C: Oxidative ring opening of 3-aryl-3-hydroxyindolones

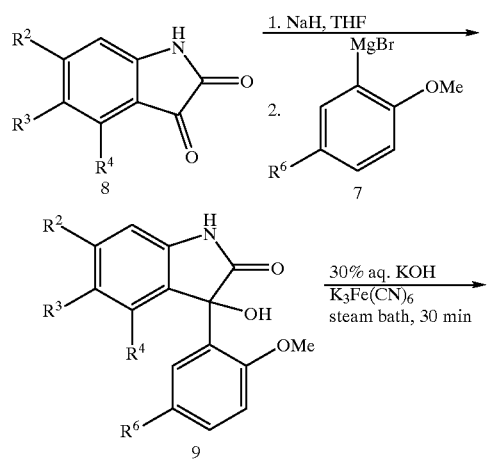

The 3-aryl-3-hydroxyindolones (9) were generated by addition of an aryl Grignard reagent (7) to isatins (8). It has been reported that oxidative ring opening of the 3-aryl-3-hydroxyindolone nucleus with either basic hydrogen peroxide or basic potassium ferricyanide generates 2-aminobenzophenones. Attempted oxidative ring opening of 3-aryl-3-hydroxyindolones under basic conditions using either hydrogen peroxide or tert-butylhydroperoxide were not successful. Upon treatment of 3-aryl-3-hydroxyindolones (9) with $K_3Fe(CN)_6$ in 30% aqueous KOH followed by heating on a steam bath for about 20–30 min quite readily opened the indolone nucleus to provide the desired 2-aminobenzophenones 4a.

Scheme 1.4

Method D: Curtius rearrangement of benzophenone-2-carboxylic acids

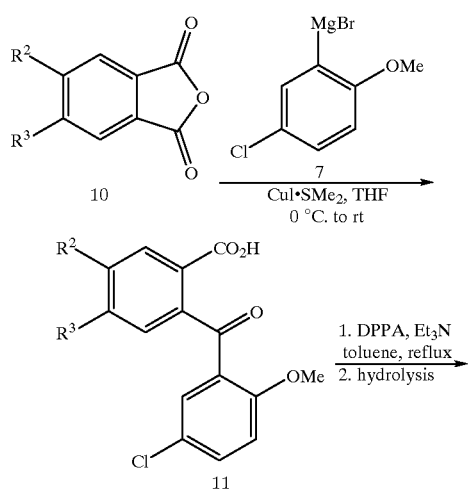

Curtius rearrangement of benzophenone-2-carboxylic acid (11) followed by hydrolysis of the intermediate isocyanate was used to generate 2-aminobenzophenones (4b). The requisite benzophenone-2-carboxylic acids (11) were prepared by addition of an aryl Grignard reagent (7) to a symmetrically substituted phthalic anhydride derivatives (10). The monoaddition of the aryl Grignard reagent can be accomplished by either carrying out the reaction at low temperature or complexing with CuI.SMe$_2$ complex. Curtius rearrangement of 11 using DPPA/Et$_3$N in refluxing toluene followed by hydrolysis of the intermediate isocyanate gave the desired 2-aminobenzophenones 4b.

General method for the preparation of 3-aminoguinolone-2 (1H)-one

As illustrated in Reaction Scheme 2, acylation of 2-aminobenzophenones (4) with haloacetyl halide in the presence of anhydrous pyridine gave the corresponding N-(haloacetyl) aminobenzophenones 12. When a solution of N-(haloacetyl) aminobenzophenone in anhydrous pyridine was heated to reflux for 15–30 min, initially formed a-pyridinium acetanilide salt undergoes cyclization followed by dehydration to afford the 3-pyridinium halide salts (13). Upon dilution of the reaction mixture with anhydrous benzene the pyridinium salts were precipitated out and were isolated by filtration. Hydrazinolysis of pyridinium salts 13 in 85% hydrazine hydrate-ethanol (6:1) at reflux for 1–2 hr provided the corresponding 3-aminoquinolones 14. The 3-aminoquinolones 14 were isolated by pouring the reaction mixture into cold water and then extracting with ether. The majority of crude 3-aminoquinolones are essentially pure and were used without further purification. Finally, demethylation of the methyl ether moiety with BBr$_3$ in methylene chloride afforded the desired phenols 15.

Reaction Scheme 2

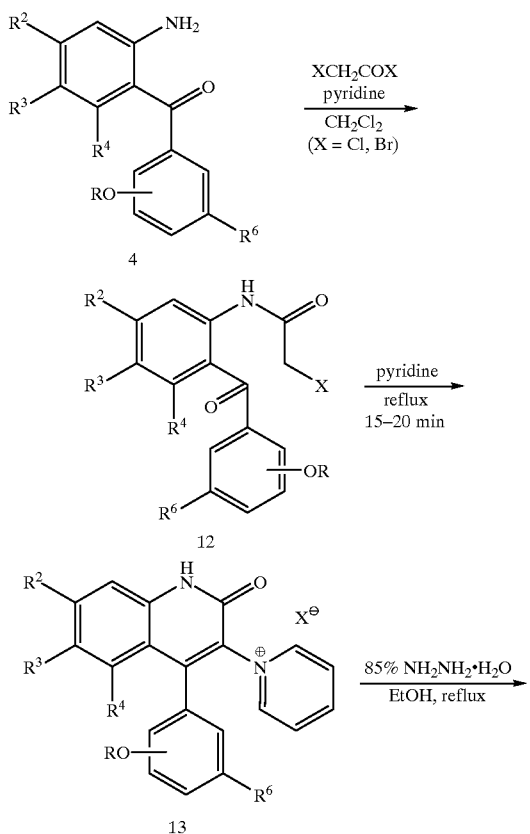

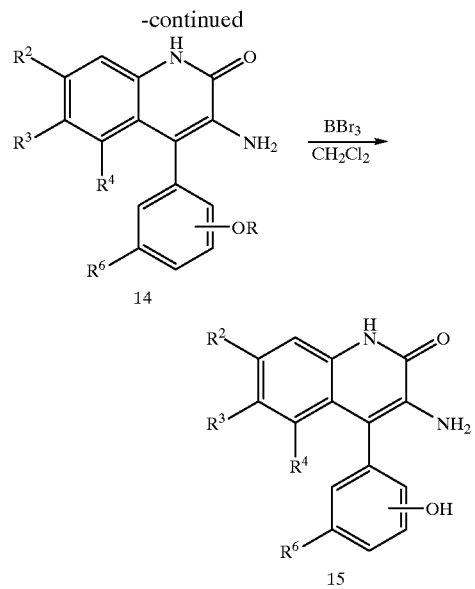

Functionalization of the 3-amino group of 3-aminoquinolin-2(1H)-ones

Selective monosulfonylation or acylation of the amino group of 16 was not possible even with limited amounts of the corresponding reagents. Instead, as illustrated in Reaction Scheme 3, either persulfonylation or peracylation of 3-aminoquinolone 16 followed by treatment with aqueous NaOH in THF afforded the desired monosulfonylated or monoacylated products 17a–d. Finally, demethylation of the methyl ether moiety of 17a–d with BBr$_3$ in methylene chloride afforded the desired phenols 18a–d.

Reaction Scheme 3

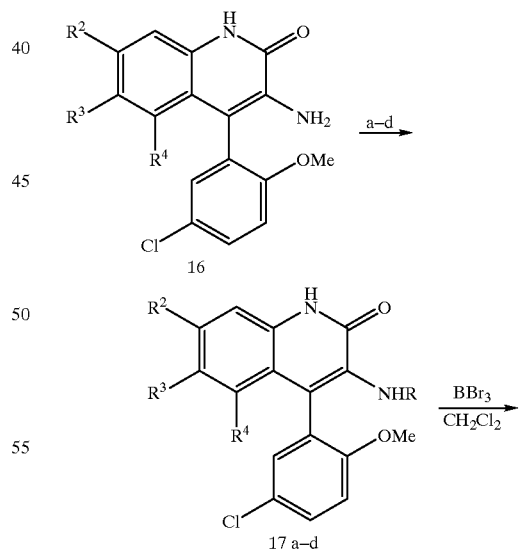

-continued

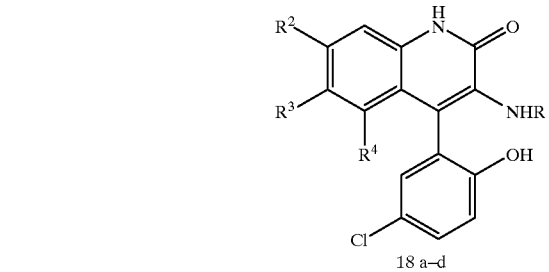

18 a–d

| R | Conditions | |
|---|---|---|
| a) SO₂CF₃ | 1. (CF₃SO₂)₂O/pyridine, r.t. | 2. 3N NaOH, THF |
| b) SO₂Me | 1. MeSO₂Cl/pyridine, heat | 2. 3N NaOH, THF |
| c) SO₂Ar | 1. ArSO₂Cl/pyridine, heat | 2. 3N NaOH, THF |
| d) COMe(Ar) | 1. Ac₂O or ArCOCl/pyridine, heat | 2. 3N NaOH, THF |

The benzyl amide analog 20 was prepared by peracylation of 19 with phenylacetyl chloride followed by selective deacetylation with 3N NaOH in MeOH-THF. The phenyl glyoxyamide analog 22 also prepared similar manner as shown in Reaction Scheme 4. The benzyl carbamate 21 was prepared by reacting 19 with excess CBz-Cl and triethylamine in refluxing dichloroethane followed by treatment with 3N NaOH in methanol.

Reaction Scheme 4

Reaction Scheme 5

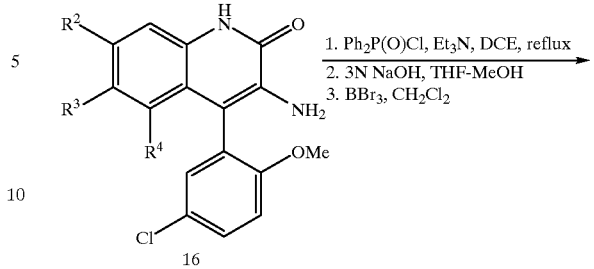

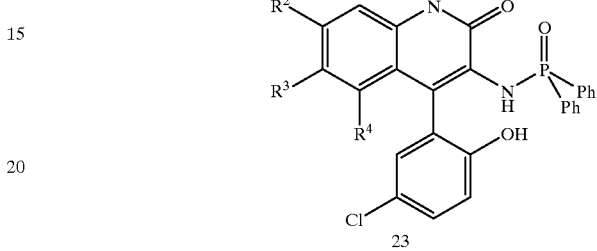

N-benzylation of 3-amino moiety of 3-aminoquinolin-2 (1H)-ones

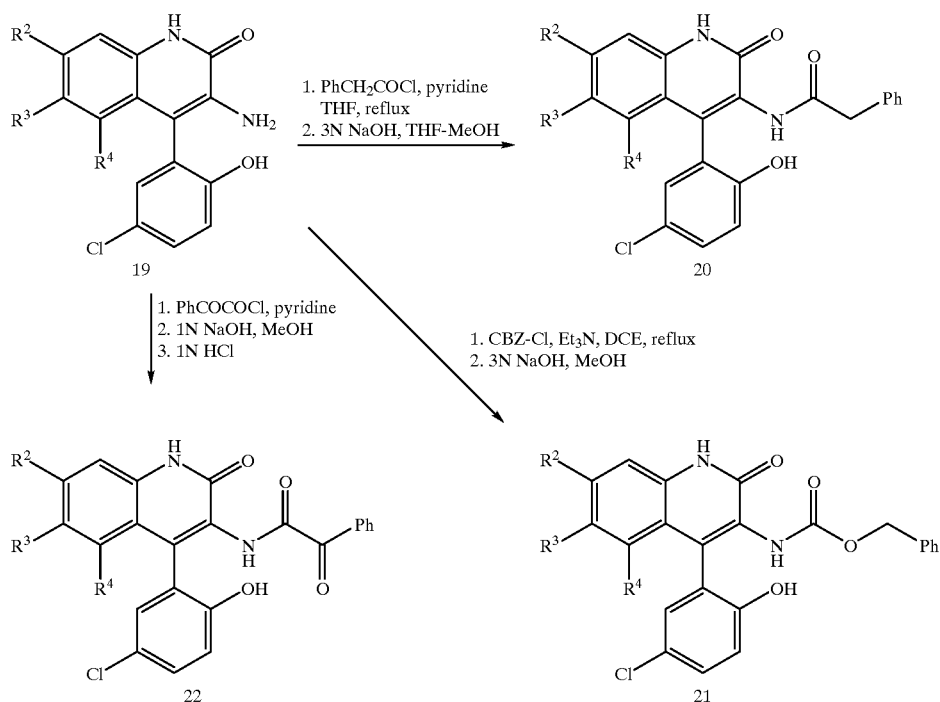

In Reaction Scheme 5, reaction of 16 with excess diphenyl phosphinyl chloride and triethylamine in refluxing DCE followed by treatment of the crude product with 3N NaOH in MeOH-THF gave the corresponding phosphinamide. Demethylation of the methyl ether intermediate with BBr₃ gave the desired phosphinamide 23.

As illustrated in Reaction Scheme 6, upon reaction of 19 with an aromatic aldehyde in refluxing toluene with removal of water formed the cyclic acetaminal intermediate 24. After removal of the toluene the crude 24 was reduced directly with NaBH₄ in methylene chloride to provide the desired benzylamines 25.

Reaction Scheme 6

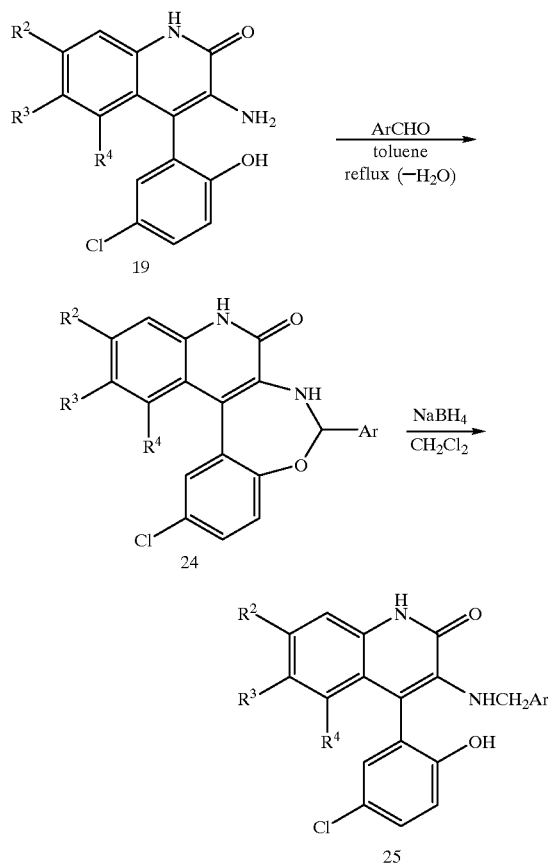

Preparation of N-Aryl-3-aminoquinolin-2(1H)-ones

Acylation of 4c with bromoacetyl bromide gave the bromoacetanilide 26, as shown in Reaction Scheme 7. Reaction of 26 with the sodium salt of N-Boc aniline in THF gave 27. After addition of another equivalent of NaH, the reaction mixture was allowed to warm to room temperature and maintained overnight. Under these conditions the intermediate 27 was cyclized and dehydrated to the desired quinolone. Upon treatment of the reaction mixture with 1 N HCl, the Boc group was deprotected to afford the quinolone 28, wherein $R^8$=hydroxyl, methoxy or amino.

Reaction Scheme 7

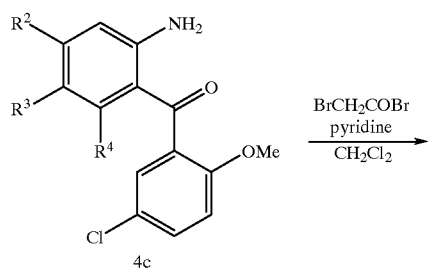

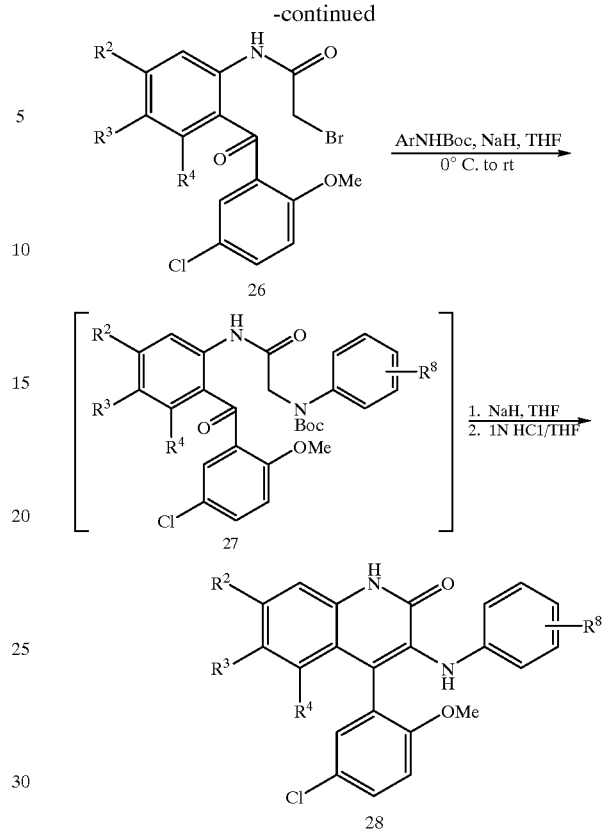

Another approach to synthesize the N-arylated 3-aminoquinolones involved direct N-arylation of the 3-amino moiety with triarylbismuth as shown in Scheme 8.

Reaction Scheme 8

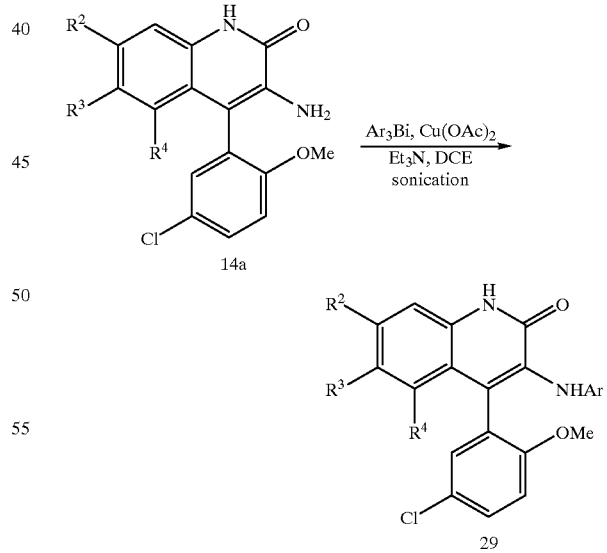

N-Alkylation of 3-aminoquinolin-2(1H)-ones

As illustrated in Reaction Scheme 9, reaction of the 3-amino moiety of 16 with a solution of the desired aldehyde and titanium isopropoxide in THF gave an intermediate which was reduced with an excess of sodium borohydride to yield the corresponding alkylated amine 30, wherein $R^9$ represents optionally substituted phenyl, pyridyl, furanyl, imidazolyl, pyrrolyl, thienyl or cyclohexyl.

Reaction Scheme 9

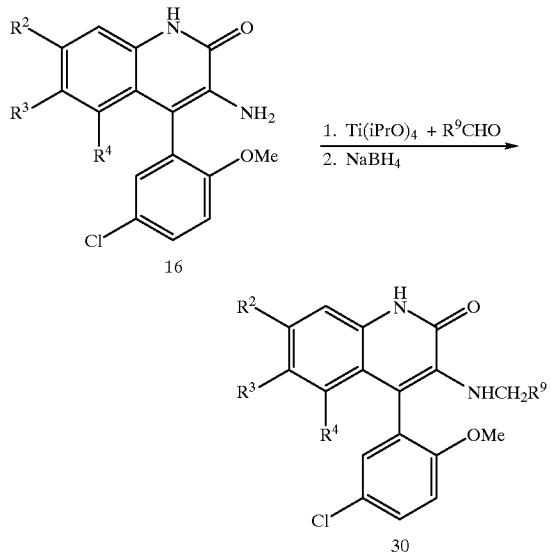

In a preferred embodiment of the invention the compounds of Formula II have the formula

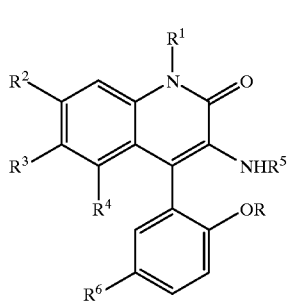

II wherein R and $R^1$ each are independently hydrogen or methyl; $R^2$, $R^3$ and $R^4$ each are independently hydrogen, chloro, nitro or trifluoromethyl; $R^5$ is hydrogen, $C_{1-4}$ alkyl, $C_{1-4}$ alkylsulfonyl, trifluoromethylsulfonyl, cyclohexylmethyl, pyridylmethyl, furanylmethyl, furanyl-2-propenyl, imidazolylmethyl, thienylmethyl, 1-methyl pyrrolylmethyl, unsubstituted or substituted phenyl, phenylmethyl, phenylcarbonyl or phenylsulfonyl wherein said phenyl substituent is selected from one or two fluoro, hydroxy, trifluoromethyl, methoxy, methylthio and nitro; and $R^6$ is chloro; or a nontoxic pharmaceutically acceptable salt thereof.

In another preferred embodiment of the invention the compound of Formula II include those wherein R is hydrogen; $R^1$ is hydrogen or methyl; $R^2$, $R^3$ and $R^4$ each are independently chloro, nitro or trifluoromethyl; $R^5$ is hydrogen, methyl, $C_{1-4}$ alkylsulfonyl, trifluoromethylsulfonyl, unsubstituted or substituted phenyl, phenylmethyl, phenylmethyl, phenylcarbonyl or phenylsulfonyl wherein said phenyl substituent is selected from one or two fluoro, hydroxy, trifluoromethyl, methoxy, methylthio and nitro; and $R^6$ is chloro; or a nontoxic pharmaceutically acceptable salt thereof.

In another aspect, this invention provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt thereof. Preferably, the compounds of Formula I are useful in the treatment of ischemia, convulsions, asthma, irritable bowel syndrome, migraine, traumatic brain injury, male erectile dysfunction, and urinary incontinence and other disorders sensitive to BK channel activating activity.

In still another aspect, this invention provides pharmaceutical compositions comprising at least one compound of Formula I in combination with a pharmaceutical adjuvant, carrier or diluent.

Biological Activity

Potassium ($K^+$) channels are structurally and functionally diverse families of $K^+$-selective channel proteins which are ubiquitous in cells, indicating their central importance in regulating a number of key cell functions [Rudy, B., Neuroscience, 25: 729–749 (1988)]. While widely distributed as a class, $K^+$ channels are differentially distributed as individual members of this class or as families. [Gehlert, D. R., et al., Neuroscience, 52: 191–205 (1993)]. In general, activation of $K^+$channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of $K^+$channels, the large-conductance $Ca^{2+}$-activated $K^+$ channels (Maxi-K or BK channels), is regulated by transmembrane voltage, intracellular $Ca^{2+}$, and a variety of other factors such as the phosphorylation state of the channel protein. [Latorre, R., et al., Ann. Rev. Pysiol., 51: 385–399 (1989)]. The large, single channel-conductance (generally>150 pS) and high degree of specificity for $K^+$ of BK channels indicates that small numbers of channels could profoundly affect membrane conductance and cell excitability. Additionally, the increase in open probability with increasing intracellular $Ca^{2+}$ indicates involvement of BK channels in the modulation of $Ca^{2+}$-dependent phenomena such as secretion and muscular contraction. [Asano, M., et al., J. Pharmacol. Exp. Ther., 267: 1277–1285 (1993)].

Openers of BK channels exert their cellular effects by increasing the open probability of these channels [McKay, M. C., et al., J. Neurophysiol., 71: 1873–1882 (1994); and Olesen, S. -P., Exp. Opin. Invest. Drugs, 3: 1181–1188 (1994)]. This increase in the opening of individual BK channels collectively results in the hyperpolarization of cell membranes, particularly in depolarized cells, produced by significant increases in whole-cell BK-mediated conductance.

The ability of compounds described in the present invention to open BK channels and increase whole-cell outward ($K^+$) BK-mediated currents was assessed under voltage-clamp conditions by determining their ability to increase cloned mammalian (mSlo or hSlo) BK-mediated outward current heterologously expressed in Xenopus oocytes [Butler, A., et al., Science, 261: 221–224 (1993); and Dworetzky, S. I., et al., Mol. Brain Res., 27: 189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., *J. Biol. Chem.,* 265: 11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compounds profiled did not effect non-BK native currents in the oocytes. All compounds were tested in at least 5 oocytes and are reported at the single concentration of 20 μM; the effect of the selected compounds of Formula I on BK current was expressed as the percent of control IBTX-sensitive current and is listed in Table I. Recordings were accomplished using standard two-electrode voltage clamp techniques [Stuhmer, W., et al., *Methods in Enzymology,* Vol. 207: 319–339 (1992)]; voltage-clamp protocols consisted of 500–750 ms duration step depolarizations from a holding potential of −60 mV to +140 mV in 20 mV steps. The experimental media (modified Barth's solution) consisted of (in mM): NaCl (88), NaHCO3 (2.4), KCl (1.0), HEPES (10), MgSO4 (0.82), Ca(NO3)2 (0.33), CaCl2 (0.41); pH 7.5.

TABLE 1

Effect of Selected Compounds on BK Channels

| Ex. No | BK Current* |
|---|---|
| 2 | ++ |
| 5 | ++ |
| 10 | + |
| 14 | + |
| 17 | ++ |
| 19 | ++ |
| 29 | + |
| 32 | + |
| 43 | + |
| 44 | + |
| 64 | ++ |
| 66 | ++ |
| 68 | + |
| 71 | + |

*at 20 μM expressed as percent increase over BK current in controls
+ = 100–150%
++ = > 150%

To determine the ability of these compounds to reduce cell loss resulting from neuronal ischemia, a standard rodent model of permanent focal ischemia, involving occlusion of the middle cerebral artery in the spontaneously hypertensive rat (MCAO model) was employed [Tamura, A., et al., *Journal of Cerebral Blood Flow and Metabolism,* Volume 1, 53–60, (1981)].

Selected compounds have been evaluated in the focal stroke model involving permanent middle cerebral artery occlusion (MCAO) in the spontaneously hypertensive rat. This procedure results in a reliably large neocortical infarct volume that is measured by means of vital dye exclusion in serial slices through the brain 24 hours after MCAO. In the present test, compounds were administered using an intravenous route of administration at 30 minutes after occlusion. For example, in this model, the compound of Example 2 reduced the cortical infarct volume by about 14% when administered (0.001 mg/kg) as a single bolus 30 minutes after middle cerebral artery occlusion as compared to vehicle-treated (2% DMSO, 98% propylene glycol) control.

The results of the above biological tests demonstrates that the compounds of the instant invention are potent openers of the large-conductance calcium-activated $K^+$ channels (Maxi-K or BK channels). Thus, the compounds of the present invention are useful for the treatment of human disorders arising from dysfunction of cellular membrane polarization and conductance and, preferably, are indicated for the treatment of ischemia, stroke, convulsions, epilepsy, asthma, irritable bowel syndrome, migraine, traumatic brain injury, spinal cord injury, male erectile dysfunction, and urinary incontinence and other disorders sensitive to BK channel activating activity.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences,* Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that a the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 µg/kg to 10 mg/kg body weight. For parenteral administration, the dose may be in the range of 0.1 µg/kg to 1 mg/kg body weight for intravenous administration The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a Gallenkamp capillary melting point apparatus are uncorrected. Proton magnetic resonance ($^1$H NMR) spectra were recorded on a Bruker AC 300 spectrometer. All spectra were determined in the solvents indicated and chemical shifts are reported in 6 units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 $cm^{-1}$ to 400 $cm^{-1}$, calibrated to 1601 $cm^{-1}$ absorption of a polystyrene film and reported in reciprocal centimeters ($cm^{-1}$). Low resolution mass spectra (MS) and the apparent molecular weight ($MH^+$)or $(M-H)^-$ was determined on a Finnigan TSQ 7000. The element analyses are reported as percent by weight.

The following procedures Nos. 1–6 illustrate representative general procedures for the preparation of intermediates and methods for the preparation of products according to this invention. It should also be evident to those skilled in the art that appropriate substitution of both the materials and methods disclosed herein will produce the examples illustrated below and those encompassed by the scope of this invention.

Procedure 1
General procedure for the metalation of (trifluoromethyl) anilines Tert-BuLi (2.2–2.4 eqt.) was added to a cold (−78° C.) stirred solution of N-Boc or N-pivaloyl protected aniline (1.0 eqt.) in anhydrous THF (~1 molar) under nitrogen. The resultant mixture was warmed to −45°–40° C. and maintained for 2–3 hrs. The resultant suspension or solution of the dianion was cooled to −78° C. and neat dry methyl 5-chloro-2-methoxybenzoate (1.1 eqt.) was added rapidly. The resultant solution was warmed to −40° C. and maintained for 1 hr. The reaction was diluted with ether and quenched with 1 N HCl and then allowed to warm to room temperature. The organic layer was separated, washed with water, brine and then dried ($Na_2SO_4$). The crude isolated product was purified by either recrystallization or trituration or silica gel flash column chromatography.

Procedure 2
General procedure for N-acylation and N-alkoxycarbonylation of 3-aminoguinolinones Neat acyl chloride or acyl anhydride or alkyl chloroformate (3–4 eqt.) was added to a cold (0–5° C.) solution of 3-aminoquinolin-2(1H)-one (1 eqt.) and anhydrous pyridine (5 eqt.) in anhydrous $CH_2Cl_2$. The reaction mixture was allowed to warm to ambient temperature and then heated to reflux for several hours until the reaction is complete. The reaction was cooled in an ice bath and quenched with 1 N NaOH solution for 0.5 hr and then acidified with 1 N HCl. The product was extracted with $CH_2Cl_2$ and washed with brine and then dried ($MgSO_4$). The crude product was purified by either recrystallization or trituration or flash column chromatography.

Procedure 3
General procedure for N-sulfonylation of 3-aminoguinolinones

Neat alkyl or aryl sulfonyl chloride (3–4 eqt.) was added to a cold (0–5° C.) solution of 3-aminoquinolin-2(1H)-one (1 eqt.) and anhydrous pyridine (5 eqt.) in anhydrous THF. The reaction mixture was allowed to warm to ambient temperature and the progress of the reaction was followed by TLC. The reaction was cooled in an ice bath and quenched with 3N NaOH solution for 0.5–1 hr and then acidified with 1 N HCl. The product sulfonamide was extracted with ether, washed with brine and then dried ($Na_2SO_4$). The crude sulfonamide was purified by either recrystallization or trituration or flash column chromatography.

Procedure 4
General procedure for the synthesis of N-arylated 3-aminoguinolinones Sodium hydride (2.2 eqt.) was added to a cold (0° C.) solution of the N-boc-aniline (2 eqt.) in anhydrous THF. The mixture was stirred for 30 min and then a THF solution of N-[2-[(5-chloro-2-methoxyphenyl) carbonyl]-4-(trifluoromethyl)phenyl]bromoacetamide (1 eqt.) was added. The mixture was allowed to warm to room temperature and stirred for 24- 48 hrs. The reaction was acidified with 1 N HCl and then stirred for 30 min. After neutralization with satd. $NaHCO_3$ the product was extracted with ether, washed with brine and then dried ($Na_2SO_4$). The crude product was purified by flash column chromatography.

Procedure 5
General procedure for N-benzylation of 3-aminoquinolinones

A stirred mixture of 3-amino-4-(5-chloro-2-hydroxyphenyl)-6-(trifluoromethyl)-1H-quinolin-2-one and excess benzaldehyde in anhydrous toluene was heated to reflux for 3–4 hrs. Then toluene was rotary evaporated and the resultant residue was dissolved in anhydrous $CH_2Cl_2$ and then treated with excess sodium triacetoxyborohydride. The mixture stirred overnight and carefully quenched with 1 N HCl and then neutralized with satd. $NaHCO_3$. The organic layer was separated, washed with brine and then dried ($MgSO_4$). The crude product was purified by flash chromatography.

Procedure 6
General procedure for N-substituted methylation of 3-aminoquinolinones A solution of aldehyde (2 eq., 2.72 mmol) and titanium isopropoxide (0.81 mL, 2.72 mmol) was stirred for one hour under nitrogen. A solution of 3-amino-4-(5-chloro-2-methoxyphenyl)-6-(trifluoromethyl)quinolin-2(1H)-one (500 mg. 1.36 mmol) and dry THF (4 mL) was then added and stirred and monitored by thin layer chronotography. If the reaction showed less than 50% of the starting material remaining by thin layer chromatography, it was taken on to the reduction procedure. Otherwise the reaction was heated to 65° C. for 24 hours before proceeding.

The reaction mixture was diluted with absolute ethanol and heated to reflux. An excess of sodium borohydride (6 eq.) was added and refluxed for three hours. After cooling, the reaction was quenched with 1 N hydrochloric acid and the resulting solids were collected by filtration. The solids were washed several times with methylene chloride and combined with the filtrate. The filtrate was concentrated and the resulting material chromatographed on silica gel affording the desired product.

EXAMPLE 1

3-Amino-4-(5-chloro-2-methoxyphenyl)-6-(trifluoromethyl)quinolin-2(1H)-one

Step A. N-[2-[(5-Chloro-2-methoxyphenyl)carbonyl]-4-(trifluoromethyl)phenyl]aminocarboxylic acid, 1,1-dimethylethyl ester A stirred neat mixture of 4-aminobenzotrifluoride (35 g, 0.218 mol) and $(Boc)_2O$ (52.4 g, 0.24 mol) was heated at 80° C. for 2–3 hours until $CO_2$ evolution ceased. The mixture was allowed to cool and the $^tBuOH$ was rotary evaporated. The resultant white solid was recrystallized from hexanes/ether to provide white needles (50.6 g, 89%) of N-(tert-butoxycarbonyl)-4-aminobenzotrifluoride.

Tert-BuLi (130 mL, 0.22 mol, 1.7M in cyclohexane) was added over 20 minutes to a cold (−78° C.) stirred solution of N-Boc-4-aminobenzotrifluoride (26.2 g, 0.1 mol) in dry THF (130 mL) under argon. The resultant yellow partial solution was warmed to −450–40° C. and maintained for 2 hrs. The resultant thick yellow slurry of the dianion was cooled to −78° C. and neat dry methyl 5-chloro-2-methoxybenzoate (22.1 g, 0.11 mol) was added rapidly. The resultant yellow-brown solution was warmed to −40° C. and maintained for 1 hr. The reaction was diluted with ether (200 mL) and quenched with 1 N HCl (250 mL) and then allowed to warm to room temperature. The organic layer was separated, washed with water, brine and then dried ($Na_2SO_4$). Evaporation of solvents gave a light-yellow solid (49.9 g) which was triturated with ether to afford 31.9 g of pure desired titled compound: mp 148–150° C.; IR (KBr, $cm^{-1}$) 3280, 1725,1640,1530,1320,1250,1150; $^1H$ NMR (300 MHz, DMSO-$d_6$)δ 1.41 (9H, s), 3.58 (3H, s), 7.19 (1H, d, J=8.9 Hz), 7.49 (1H, d, J=2.7 Hz), 7.58 (1H, d, J=2.6 Hz), 7.60 (1H, dd, J=8.9 and 2.7 Hz), 7.93 (1H, dd, J=8.7 and 1.9 Hz), 8.12(1H, s), 8.15(1H, m), 10.35(1H, s); MS m/e 430 (MH$^+$).

Anal. calcd. for $C_{20}H_{19}ClF_3NO_4$: C, 55.88;H, 4.45; N, 3.25. Found: C, 55.51;H, 4.38; N, 3.26.

Step B. 1-[2-Amino-5-(trifluoromethyl)phenyl]-1'-(5-chloro-2-methoxyphenyl)methanone To a stirred solution of N-[2-[(5-chloro-2-methoxyphenyl)carbonyl]-4-(trifluoromethyl)phenyl]aminocarboxylic acid, 1,1-dimethylethyl ester (19 g, 0.044 mol) in ethanol (300 mL), 3N HCl was added. The resultant suspension was heated to reflux for 3 hrs. The progress of the hydrolysis was monitored by TLC. The reaction mixture was cooled and poured into cold water (500 mL). The product was extracted with ether (2×200 mL) and the combined ether extracts were washed with water, brine and then dried ($Na_2SO_4$). Evaporation of the ether gave a golden yellow viscous oil which upon standing overnight solidified to afford a beige solid (14.6 g, 100%): mp 90–92° C.; IR (KBr, $cm^{-1}$) 3340,3470,1640,1320,1240,1150, 1025; $^1H$ NMR (300 MHz, DMSO-$d_6$)δ 3.68 (3H, s), 6.97 (1H, d, J=8.8 Hz), 7.19 (1H, d, J=8.9 Hz), 7.26 (1H, d, J=1.1 Hz), 7.36 (1H, d, J=2.7 Hz), 7.53 (2H, m), 7.92 (2H, brd s); MS m/e 330 (MH$^+$).

Anal. calcd. for $C_{15}H_{11}ClF_3NO_2$:C, 54.64;H, 3.36; N, 4.25. Found: C, 54.65;H, 3.37; N, 4.16.

Step C. N-[2-[(5-Chloro-2-methoxyphenyl)carbonyl]-4-(trifluoromethyl)phenyl]chloroacetamide A solution of chloroacetyl chloride (5.1 mL, 0.053 mol) in anhydrous $CH_2Cl_2$ (20 mL) was added dropwise over 15–20 min to a stirred cold (0° C.) solution of 1-[2-amino-5-(trifluoromethyl)phenyl]-1'-(5-chloro-2-methoxyphenyl) methanone (14.6 g, 0.044 mol) and anhydrous pyridine (4.3 mL, 0.053 mol) in $CH_2Cl_2$ (80 mL). The resultant mixture was allowed to warm to room temperature and maintained for 1 hr. The reaction was acidified with 1 N HCl (50 mL). The organic layer was separated and washed consecutively with satd. $NaHCO_3$, water, brine and then dried ($MgSO_4$). Evaporation of the $CH_2Cl_2$ gave a beige solid (18.7 g). The crude product was triturated with ether to afford an off-white solid (16.23 g, 91%): mp 136–137° C.; IR (KBr, $cm^{-1}$) 1694, 1644, 1522,1314,1124; $^1H$ NMR (300 MHz, CDCl$_3$)δ 3.67 (3H, s), 4.23 (2H, s), 6.93 (1H, d, J=8.8 Hz), 7.38 (1H, d, J=2.6 Hz), 7.48 (1H, dd, J=8.8 and 2.6 Hz), 7.69 (1H, s), 7.79 (1H, d, J=8.8 Hz), 8.87 (1H, d, J=8.8 Hz), 12.30 (1H, s); MS m/e 404 (M-H)$^-$.

Step D. 1-[4-(5-Chloro-2-methoxyphenyl)-2-oxo-6-(trifluoromethyl)-1H-quinolin-3-yl]pyridinium, chloride A mechanically stirred solution of N-[2-[(5-chloro-2-methoxyphenyl)carbonyl]-4-(trifluoromethyl)phenyl] chloroacetamide (12.2 g, 0.03 mol) in anhydrous pyridine (150 mL) was heated to reflux for 20–25 min. The resultant suspension of the pyridinium salt was allowed to cool and then diluted with benzene (100 mL). The pyridinium salt was filtered, washed with benzene and then dried in vacuo to afford the desired titled compound (13.75 g, 98%): mp 325–330° C. (dec.); IR (KBr, $cm^{-1}$) 1678,1322,1270,1118; $^1H$ NMR (300 MHz, DMSO-$d_6$)δ 3.59 (3H, s), 7.09 (1H, d, J=9.0 Hz), 7.38 (1H, s), 7.44 (1H, d, J=2.6 Hz), 7.52 (1H, dd, J=8.9 and 2.6 Hz), 7.83 (1H, d, J=8.7 Hz), 8.11 (1H, dd, J=8.7 and 1.8 Hz), 8.19–8.27 (2H, m), 8.70–8.75 (1H, m), 9.05–9.07 (2H, m), 13.54 (1H, brd s); MS m/e 431 (MH)$^+$.

Anal. calcd. for $C_{22}H_{15}Cl_2F_3N_2O_2 \cdot 0.33H_2O$: C, 55.84;H, 3.34; N, 5.92. Found: C, 55.83;H, 3.33; N, 5.84.

Step E. 3-Amino-4-(5-chloro-2-methoxyphenyl)-6-(trifluoromethyl)quinolin-2(1H)-one Hydrazine (25 mL, 85%w/w) was added to a stirred suspension of 1-[4-(5-chloro-2-methoxyphenyl)-2-oxo-6-(trifluoromethyl)-1H-quinolin-3-yl]pyridinium, chloride (13.5 g, 0.029 mol) in ethanol (150 ml). The resultant red-brown solution was heated to reflux for 1.5 hrs. The reaction mixture was allowed to cool to room temperature and then poured into cold water (300 mL). The precipitated product was extracted with ether (2×200 mL). The combined ether extracts were washed wth water (200 mL), brine (100 mL) and then dried ($Na_2SO_4$). Evaporation of the ether gave an off-white solid (10.80 g) which was triturated with ether/hexanes to afford the desired titled compound (10.6 g, 99%): mp 246–248° C. (dec.); IR (KBr, $cm^{-1}$) 3400,1668, 1332,1284,1118; $^1$H NMR (300 MHz, DMSO-$d_6$)δ 3.66 (3H, s), 5.24 (2H, brd s), 6.87 (1H, s), 7.22 (1H, d, J=2.6 Hz), 7.24 (1H, d, J=8.8 Hz), 7.40 (1H, d, J=8.5 Hz), 7.45 (1H, d, J=8.5 Hz), 7.51 (1H, dd, J=8.8 and 2.6 Hz), 12.31 (1H, brd s); MS m/e 369 (MH)$^+$.

Anal. calcd. for $C_{17}H_{12}ClF_3N_2O_2$: C, 55.37;H, 3.28; N, 7.60. Found: C, 55.26;H, 3.46; N, 7.53.

EXAMPLE 2

3-Amino-4-(5-chloro-2-hydroxyphenyl)-6-(trifluoromethyl)quinolin-2(1H)-one

A boron tribromide solution in $CH_2Cl_2$ (1M, 12 mL 12 mmol) was added to a cold (–20° C.) stirred suspension of 3-amino-4-(5-chloro-2-methoxyphenyl)-6-(trifluoromethyl)-2-(1H)-quinolone (1.47 g, 3 mmol) in anhydrous $CH_2Cl_2$ (20 mL) under nitrogen. The reaction flask was closed with a glass stopper and the mixture was stirred at room temperature for 6–8 hrs. The progress of the demethylation was monitored by TLC. The reaction was quenched with 1 N NaOH (36 mL) and then the pH of the aqueous phase was adjusted to 7 with either satd. $NaHCO_3$ or 1 N HCl. Since the product was not completely soluble in $CH_2Cl_2$, the $CH_2Cl_2$ layer was separated and rotary evaporated at room temperature. The organic residue was dissolved in EtOAc (50 mL) and combined with the aqueous layer in the separatory funnel. The product was completely extracted into the EtOAc and washed with water, brine and then dried ($Na_2SO_4$). Evaporation of the EtOAc gave a light-brown semi-solid (1.53 g) which was triturated with $CH_2Cl_2$ to afford the titled compound as a beige solid (1.38 g, 97%): mp 233–235° C.; IR (KBr, $cm^{-1}$) 3300,1670,1330, 1280, 1122; $^1$H NMR (300 MHz, DMSO-$d_6$)δ 5.15 (2H, brd s), 6.96 (1H, s), 7.03(1H, d, J=8.7 Hz), 7.14(1H, d, J=2.6 Hz), 7.33(1H, dd, J=8.7 and 2.6 Hz), 7.40 (1H, d, J=8.4 Hz), 7.46 (1H, d, J=8.6 Hz), 9.69 (1H, s), 12.28 (1H, s); MS m/e 355 (MH)$^+$.

EXAMPLE 3

3-Amino-4-(5-chloro-2-methoxyphenyl)-7-(trifluoromethyl)quinolin-2(1H)-one mp 245–248° C. (dec.); IR (KBr, $cm^{-1}$) 3368,1664,1316, 1234, 1120; $^1$H NMR (300 MHz, CDCl$_3$)δ 3.56 (3H, s), 4.39 (2H, brd s), 6.89 (2H, m), 7.07–7.09 (2H, m), 7.26–7.29 (1H, m), 7.43 (1H, s), 12.04 (1H, brd s); MS m/e 367 (M-H)$^-$.

Anal. calcd. for $C_{17}H_{12}ClF_3N_2O_2$: C, 55.37;H, 3.28; N, 7.60. Found: C, 55.32;H, 3.13; N, 7.77.

EXAMPLE 4

3-Amino-4-(5-chloro-2-hydroxyphenyl)-7-(trifluoromethyl)quinolin-2(1H)-one mp 225–227° C.; IR (KBr, $cm^{-1}$)3350,1666,1318,1254, 1126; $^1$H NMR (300 MHz, DMSO-$d_6$)δ 5.27 (2H, brd s), 6.90 (1H, d, J=8.4 Hz), 7.02 (1H, d, J=8.7 Hz), 7.11 (1H, d, J=2.6 Hz), 7.27–7.34 (2H, m), 7.54 (1H, s), 9.64 (1H, s), 12.20 (1H, s); MS m/e 355 (MH)$^+$.

EXAMPLE 5

N-[4-(5-Chloro-2-hydroxyphenyl)-2-oxo-6-(trifluoromethyl)-1H-quinolin-3-yl] trifluoromethanesulfonamide mp 268–270° C.; IR (KBr, $cm^{-1}$) 1118,1206,1280,1322, 1650, 3180; $^1$H NMR (300 MHz, DMSO-$d_6$)δ 7.00 (1H, d, J=8.7 Hz), 7.18 (1H, d, J=2.5 Hz), 7.31 (1H, s), 7.38 (1H, dd, J=8.7 and 2.5 Hz), 7.55 (1H, d, J=8.6 Hz), 7.88 (1H, d, J=8.6 Hz), 10.09 (1H, brd s), 12.63 (1H, s); MS m/e 487 (MH)$^+$.

Anal. calcd. for $C_{17}H_9ClF_6N_2O_4S$: C, 41.95;H, 1.86; N, 5.75. Found: C, 41.46;H, 1.95; N, 5.57.

EXAMPLE 6

N-[4-(5-Chloro-2-hydroxyphenyl)-2-oxo-7-(trifluoromethyl)-1H-quinolin-3-yl] trifluoromethanesulfonamide mp 267–270° C.; IR (KBr, $cm^{-1}$) 1134,1220,1328,1644, 2500–3600; $^1$H NMR (300 MHz, DMSO-$d_6$)δ 6.98 (1H, d, J=8.7 Hz), 7.15 (1H, d, J=2.6 Hz), 7.27 (1H, d, J=8.5 Hz), 7.36 (1H, dd, J=8.7 and 2.6 Hz), 7.45 (1H, d, J=8.6 Hz), 7.67 (1H, s), 10.0 (1H, brd s), 12.50 (1H, s); MS m/e 487 (MH)$^+$.

Anal. calcd. for $C_{17}H_9ClF_6N_2O_4S \cdot 0.5H_2O$: C, 41.16;H, 2.04; N, 5.65. Found: C, 41.15;H, 1.98; N, 5.61.

EXAMPLE 7

N-[4-(5-Chloro-2-hydroxyphenyl)-2-oxo-6-(trifluoromethyl)-1H-quinolin-3-yl]acetamide mp 222–224° C.; IR (KBr, $cm^{-1}$) 1128,1172, 1324,1672, 2100–3600; $^1$H NMR (300 MHz, DMSO-$d_6$)δ 6.98 (1H, d, J=8.7 Hz), 7.07 (1H, d, J=2.6 Hz), 7.24 (1H, s), 7.34 (1H, dd, J=8.6 and 2.6 Hz), 7.51 (1H, d, J=8.6 Hz), 7.80 (1H, d, J=8.8 Hz), 9.10 (1H, brd s), 10.0 (1H, brd s), 12.4 (1H, brd s); MS m/e 397 (MH)$^+$.

EXAMPLE 8

N-[4-(5-Chloro-2-hydroxyphenyl)-2-oxo-6-(trifluoromethyl)-1H-quinolin-3-yl] methanesulfonamide mp 263–265° C.; IR (KBr, $cm^{-1}$) 1140,1322,1662, 3400; $^1$H NMR (300 MHz, DMSO-$d_6$)δ 7.00 (1H, d, J=8.7 Hz), 7.17 (1H, d, J=2.6 Hz), 7.21 (1H, s), 7.37 (1H, dd, J=8.7 and 2.6 Hz), 7.53 (1H, d, J=8.6 Hz), 7.82 (1H, d, J=8.7 Hz), 8.78 (1H, s), 9.99 (1H, s), 12.51 (1H, s); MS m/e 431 (M-H)$^-$.

EXAMPLE 9

N-[4-(5-Chloro-2-hydroxyphenyl)-2-oxo-6-(trifluoromethyl)-1H-quinolin-3-yl] phenylsulfonamide mp 262–265° C.; IR (KBr, $cm^{-1}$) 1116, 1170,1280,1322, 1340, 1660, 3474; $^1$H NMR (300 MHz, DMSO-$d_6$)δ 6.85 (1H, d, J=8.7 Hz), 7.08 (1H, d, J=2.6 Hz), 7.22 (2H, m), 7.39 (2H, m), 7.51 (2H, m), 7.58 (2H, m), 7.80 (1H, d, J=6.8 Hz), 9.2 (1H, brd s), 9.9 (1H, brd s), 12.38 (1H, s); MS m/e 495 (MH)$^+$.

EXAMPLE 10

N-[4-(5-Chloro-2-hydroxyphenyl)-2-oxo-6-(trifluoromethyl)-1H-quinolin-3-yl]benzamide mp 309–311° C. (dec.); IR (KBr, $cm^{-1}$) 1122,1270,1322, 1504, 1654, 3192; $^1$H NMR (300 MHz, DMSO-$d_6$)δ 6.96

(1H, d, J=8.7 Hz), 7.19 (1H, d, J=2.6 Hz), 7.27 (1H, dd, J=8.7 and 2.6 Hz), 7.32 (1H, s), 7.43 (2H, t, J=7.7 Hz), 7.51 (1H, d, J=7.2 Hz), 7.56 (1H, d, J=8.4 Hz), 7.74 (2H, d, J=7.1 Hz), 7.85 (1H, d, J=8.7 Hz), 9.62 (1H, s) 10.05 (1H, s), 12.51 (1H, s); MS m/e 459 (MH)$^+$.

EXAMPLE 11

4-(5-Chloro-2-hydroxyphenyl)-3-(phenylmethyl) amino-6-(trifluoromethyl)quinolin-2(1H)-one mp 215–217° C.; IR (KBr, cm$^{-1}$) 1118,1330,1646, 3300; $^1$H NMR (300 MHz, CDCl$_3$-CD3OD δ 3.80 (1H, d, J=14.3 Hz), 3.93 (1H, d, J=14.3 Hz), 6.86 (1H, d, J=8.7 Hz), 6.92 (1H, d, J=2.6 Hz), 6.99 (1H, s), 7.01 (1H, d, J=2.0 Hz), 7.11–7.28 (6H, m), 7.36 (1H, dd, J=8.5 and 1.7 Hz); MS m/e 445 (MH)$^+$.

EXAMPLE 12

3-Amino-4-(5-chloro-2-hydroxyphenyl)-5,7-dichloroquinolin-2(1H)-one mp 275–277° C.; IR (KBr, cm$^{-1}$) 1668, 3400; $^1$H NMR (300 MHz, DMSO-d$_6$)δ 5.00 (2H, s), 6.87 (1H, d, J=8.7 Hz), 7.03 (1H, d, J=2.5 Hz), 7.12 (1H, d, J=2.0 Hz), 7.24 (1H, dd, J=8.6 and 2.5 Hz), 7.29 (1H, d, J=1.7 Hz), 9.55 (1H, s), 12.28 (1H, s); MS m/e 353 (M-H)$^-$.

EXAMPLE 13

3-Amino-4-(5-chloro-2-methoxyphenyl)quinolin-2(1H)-one mp 248–250° C.; IR (KBr, cm$^{-1}$) 750,1250,1658, 3000; $^1$H NMR (300 MHz, CDCl$_3$)δ 3.72 (3H, s), 6.94 (1H, d, J=7.4 Hz), 7.02 (1H, d, J=8.9 Hz), 7.06 (1H, t, J=6.9 Hz), 7.23–7.27 (2H, m), 7.30 (1H, t, J=7.4 Hz), 7.40 (1H, dd, J=8.8 and 2.6 Hz), 11.2 (1H, brd s); MS m/e 301 (MH$^+$).

EXAMPLE 14

3-Amino-4-(5-chloro-2-hydroxyphenyl)quinolin-2(1H)-one mp 265–268° C.; IR (KBr, cm$^{-1}$) 748,1656, 3300; $^1$H NMR (300 MHz, DMSO-d$_6$)δ 4.82 (2H, s), 6.75 (1H, d, J=7.8 Hz), 6.97 (1H, t, J=7.7 Hz), 7.01 (1H, d, J=8.7 Hz), 7.08 (1H, d, J=2.6 Hz), 7.15 (1H, t, J=7.1 Hz), 7.23 (1H, d, J=7.9 Hz), 7.30 (1H, dd, J=8.7 and 2.6 Hz), 9.62 (1H, s), 11.93 (1H, s); MS m/e 287 (MH$^+$).

EXAMPLE 15

3-Amino-4-(2-hydroxyphenyl)quinolin-2(1H)-one mp 235–237° C.; IR (KBr, cm$^{-1}$) 748, 1218, 1658, 3300; $^1$H NM R (300 MHz, DMSO-d$_6$)δ 4.62 (2H, s), 6.79 (1H, d, J=8.0 Hz), 6.91–6.98 (2H, m), 7.01(1H, d, J=8.2 Hz), 7.07(1H, d, J=7.5 Hz), 7.15(1H, t, J=7.0 Hz), 7.23–7.30 (2H, m), 9.36 (1H, s), 11.91 (1H, s); MS m/e 253 (MH$^+$).

Anal. calcd. for C$_{15}$H$_{12}$N$_2$O$_2$0.22H2O: C, 70.31;H, 4.89; N, 10.93. Found: C, 70.30;H, 4.75; N, 10.88.

EXAMPLE 16

3-Amino-4-(5-chloro-2-methoxyphenyl)-5,7-dichloroquinolin-2(1H)-one mp 284–287° C.; IR (KBr, cm$^{-1}$) 1244,1666, 2100–3600; MS m/e 369 (MH$^+$).

EXAMPLE 17

N-[4-(5-Chloro-2-hydroxyphenyl)-2-oxo-6-(trifluoromethyl )-1H-quinolin-3-yl]aminocarboxylic acid, phenylmethyl ester mp 234–236° C. (dec.); IR (KBr, cm$^{-1}$) 698,1130,1324, 1498, 1652, 1690; $^1$H NMR (300 MHz, DMSO-d$_6$)δ 4.96 (1H, d, J=13.0 Hz), 5.00 (1H, d, J=13.0 Hz), 6.99 (1H, d, J=8.7 Hz), 7.12 (1H, d, J=2.6 Hz), 7.52 (1H, d, J=8.6 Hz), 7.81 (1H, d, J=8.6 Hz), 8.67 (1H, s), 9.97 (1H, s), 12.45 (1H, s); MS m/e 489 (MH$^+$).

EXAMPLE 18

3-Amino-4-(5-chloro-2-methoxyphenyl)-6-nitroquinolin-2(1H)-one mp 332–335° C. (dec.); IR (KBr, cm$^{-1}$) 1338,1588,1664; $^1$H NMR (300 MHz, DMSO-d$_6$)δ 3.69 (3H, s), 5.41 (2H, s), 7.27 (1H, d, J=2.4 Hz), 7.30 (1H, s), 7.41 (1H, d, J=8.9 Hz), 7.50 (1H, d, J=2.4 Hz), 7.56 (1H, dd, J=8.9 and 2.6 Hz), 8.02 (1H, dd, J=8.9 and 2.4 Hz), 12.56 (1H, s); MS m/e 344 (M-H)$^-$.

EXAMPLE 19

3-Amino-4-(5-chloro-2-hydroxyphenyl)-6-nitroquinolin-2(1H)-one mp 344–347° C.; IR (KBr, cm$^{-1}$) 1340,1670, 3370; $^1$H NMR (300 MHz, DMSO-d$_6$)δ 5.33 (2H, s), 7.07 (1H, d, J=8.7 Hz), 7.19 (1H, d, J=2.6 Hz), 7.38 (1H, dd, J=8.8 and 2.7 Hz), 7.43 (1H, s), 7.58 (1H, d, J=2.4 Hz), 8.03 (1H, dd, J=8.9 and 2.5 Hz), 9.76 (1H, s), 12.54 (1H, s); MS m/e 330 (M-H)$^-$.

EXAMPLE 20

N-[4-(5-Chloro-2-hydroxyphenyl)-2-oxo-6-(trifluoromethyl)-1H-quinolin-3-yl]phenylacetamide mp 278–281° C. (dec.); IR (KBr, cm$^{-1}$) 1122,1322,1656; $^1$H NMR (300 MHz, DMSO-d$_6$) 3.46 (2H, m), 6.95–7.00 (3H, m), 7.05 (1H, d, J=2.6 Hz), 7.18–7.25 (4H, m), 7.35 (1H, dd, J=8.7 and 2.7 Hz), 7.54 (1H, d, J=8.6 Hz), 7.82 (1H, d, J=8.8 Hz), 9.39 (1H, s), 9.93 (1H, s), 12.46 (1H, s); MS m/e 471 (M-H)$^-$.

EXAMPLE 21

4-(5-Chloro-2-methoxyphenyl)-3-(phenylamino)-6-(trifluoromethyl)quinolin-2(1H)-one A stirred suspension of 1 equivalent each of Example 1, triphenylbismuth, copper acetate and 2 eqts. of triethylamine in dichloroethane was sonicated for 1 hr and then stirred overnight at rt. The reaction mixture filtered through a pad of celite. The filtrate was concentrated and flash columned (silica gel/3% MeOH in methylene chloride) to afford 4-(5-chloro-2-methoxyphenyl)-3-(phenylamino)-6-(trifluoromethyl)quinolin-2(1H)-one: mp 235–240° C. (dec.); IR (KBr, cm$^{-1}$) 1124,1274,1328,1658; $^1$H NMR (300 MHz, CDCl$_3$)δ 3.67 (3H, s), 6.62 (1H, d, J=8.8 Hz), 6.75 (1H, d, J=8.0 Hz), 6.85 (2H, m), 6.98 (2H, m), 7.08 (1H, m), 7.27 (3H, m), 7.50 (1H, d, J=6.9 Hz), 11.31 (1H, s); MS m/e 443 (M-H)$^-$.

EXAMPLE 22

N-[4-(5-Chloro-2-hydroxyphenyl)-2-oxo-6-(trifluoromethyl)-1H-quinolin-3-yl] phenylglyoxyamide mp 255–260° C. (dec.); IR (KBr, cm$^{-1}$) 1132,1322,1670; $^1$H NMR (300 MHz, DMSO-d$_6$)δ 7.06 (1H, d, J=8.5 Hz), 7.22 (1H, s), 7.30 (1H, m), 7.44–7.60 (5H, m), 7.69–7.76 (2H, m), 7.87 (1H, d, J=8.8 Hz); MS m/e 485 (M-H)⁻.

EXAMPLE 23

3-Amino-4-(5-chloro-2-hydroxyphenyl)-7-nitroquinolin-2(1H)-one mp 198–201° C. (dec.); IR (KBr, cm⁻¹) 1332,1516,1664, 3368; ¹H NMR (300 MHz, DMSO-d₆)δ 5.73 (2H, s), 6.88 (1H, d, J=8.9 Hz), 7.03 (1H, d, J=8.7 Hz), 7.14(1H, d, J=2.7 Hz), 7.35(1H, dd, J=8.7 and 2.7 Hz), 7.84 (1H, dd, J=8.9 and 2.4 Hz), 8.13 (1H, d, J=2.4 Hz), 9.69 (1H, s), 12.39 (1H, s); MS m/e 330 (M-H)⁻.

EXAMPLE 24

3-Amino-4-(5-chloro-2-methoxyphenyl)-7-nitroquinolin-2(1H)-one mp 293–295° C.; IR (KBr, cm⁻¹) 1332,1520,1670; ¹H NMR (300 MHz, DMSO-d₆)δ 3.68 (3H, s), 5.81 (2H, s), 6.81 (1H, d, J=8.9 Hz), 7.22 (1H, d, J=2.7 Hz), 7.24 (1H, d, J=8.8 Hz), 7.53 (1H, dd, J=8.8 and 2.7 Hz), 7.82 (1H, dd, J=8.9 and 2.4 Hz), 8.13 (1H, d, J=2.4 Hz), 12.41 (1H, brd s); MS m/e 344 (M-H)⁻.

EXAMPLE 25

N-[4-(5-Chloro-2-hydroxyphenyl)-2-oxo-6-(trifluoromethyl)-1H-quinolin-3-yl] diphenylphosphinamide A stirred suspension of 3-amino-4-(5-chloro-2-methoxyphenyl)-6-(trifluoromethyl)-1H-quinolin-2-one (184 mg, 0.5 mmol), triethylamine (0.21 mL, 1.5 mmol) and diphenylphosphinyl chloride (355 mg, 1.5 mmol) in dichloroethane (2 mL) was heated to reflux for 4–5 hrs. The reaction was quenched with 1 N HCl and extracted with CH₂Cl₂. After evaporation of CH₂Cl₂ the resultant residue was dissolved in THF and treated with 3N NaOH for 1–2 hrs. The mixture was acidified with 1 N HCl and then extracted with ether, washed with brine and then dried (Na₂SO₄). The crude product was triturated with CH₂Cl₂ to afford pure desired phosphinamide. Demethylation of the methyl ether moiety with BBr₃ gave the desired phenolic phosphinamide: mp 257–260° C.; IR (KBr, cm⁻¹) 692, 728,1126,1190,1274,1664; ¹H NMR (300 MHz, DMSO-d₆)δ 6.82 (1H, d, J=7.5 Hz), 6.87(1H, d, J=8.7 Hz), 7.08(1H, s), 7.14(1H, d, J=2.6 Hz), 7.20 (1H, dd, J=8.7 and 2.6 Hz), 7.37–7.50 (7H, m), 7.60–7.72 (4H, m), 9.95 (1H, s), 12.42 (1H, s); MS m/e 553 (M-H)⁻.

EXAMPLE 26

3-Amino-4-(5-chloro-2-hydroxyphenyl)-5,6-dichloroquinolin-2(1H)-one mp 263–265° C.; IR (KBr, cm⁻¹) 1266,1662, 3382; ¹H NMR (300 MHz, DMSO-d₆)δ 5.06 (2H, s), 6.90 (1H, d, J=8.7 Hz), 7.06 (1H, d, J=2.6 Hz), 7.25–7.29 (2H, m), 7.39 (1H, d, J=8.7 Hz), 9.57 (1H, s), 12.31 (1H, s); MS m/e 353 (M-H)⁻.

EXAMPLE 27

3-Amino-4-(5-chloro-2-methoxyphenyl)-5,6-dichloroquinolin-2(1H)-one mp 275–278° C. (dec.); IR (KBr, cm⁻¹) 1240,1660, 3392; ¹H NMR (300 MHz, DMSO-d₆)δ 3.69 (3H, s), 5.12 (2H, s), 7.11 (1H, d, J=8.9 Hz), 7.14(1H, d, J=2.7 Hz), 7.28 (1H, d, J=8.8 Hz), 7.39 (1H, d, J=8.7 Hz), 7.45 (1H, dd, J=8.8 and 2.7 Hz), 12.34 (1H, s); MS m/e 367 (M-H)⁻.

EXAMPLE 28

N-[4-(5-Chloro-2-hydroxyphenyl)-2-oxo-6-(trifluoromethyl)-1H-quinolin-3-yl]-4-methoxybenzamide mp 285–287° C.; IR (KBr, cm⁻¹) 1076,1120,1173,1259, 1323, 1656, 2800–3400; ¹H NMR (300 MHz, DMSO-d₆)δ 3.79 (3H, s), 6.95–6.98 (3 H, m), 7.19 (1H, m), 7.28 (1H, dd, J=8.7 and 2.7 Hz), 7.32 (1H, s), 7.56 (1H, d, J=8.6 Hz), 7.76(2H, d, J=7.4 Hz), 7.84(1H, d, J=8.7 Hz), 9.45 (1H, s), 10.03 (1H, s), 12.49 (1H, s); MS m/e 489 (MH)⁺.

EXAMPLE 29

N-[4-(5-Chloro-2-hydroxyphenyl)-2-oxo-6-(trifluoromethyl)-1H-quinolin-3-yl]-4-hydroxybenzamide mp 286–289° C. (dec.); IR (KBr, cm⁻¹) 1119,1323,1654, 3194; ¹H NMR (300 MHz, DMSO-d₆)δ 6.76 (2H, d, J=8.7 Hz), 6.96 (1H, d, J=8.7 Hz), 7.18 (1H, d, J=2.6 Hz), 7.27 (1H, dd, J=8.7 and 2.7 Hz), 7.31 (1H, s), 7.55 (1H, d, J=8.6 Hz), 7.65 (2H, d, J=8.7 Hz), 7.84 (1H, d, J=8.7 Hz), 9.31 (1H, s), 10.04 (1H, s), 12.48 (1H, s); MS m/e 473 (M-H)⁻.

EXAMPLE 30

4-(5-Chloro-2-hydroxyphenyl)-3-[[(4-methoxyphenyl)methyl]amino]-6-(trifluoromethyl) quinolin-2(1H)-one mp 103–106° C.; IR (KBr, cm⁻¹) 1118, 1329,1657, 3200; MS m/e 473 (M-H)⁻.

EXAMPLE 31

N-[4-(5-Chloro-2-hydroxyphenyl)-2-oxo-6-(trifluoromethyl)-1H-quinolin-3-yl]-4-hydroxybenzenesulfonamide mp 180–185° C. (dec.); IR (KBr, cm⁻¹) 1147,1322,1662, 3233; ¹H NMR (300 MHz, DMSO-d₆)δ 6.71 (2H, d, J=8.8 Hz), 6.91 (1H, d, J=8.7 Hz), 7.10 (1H, d, J=2.6 Hz), 7.24 (1H, s), 7.27 (1H, dd, J=8.7 and 2.6 Hz), 7.42 (2H, d, J=8.8 Hz), 7.47 (1H, d, J=8.6 Hz), 7.80 (1H, d, J=8.6 Hz), 8.80 (1H, brd s), 9.92 (1H, brd s), 10.25 (1H, brd s), 12.38 (1H, s); MS m/e 511 (MH⁺).

EXAMPLE 32

N-[4-(5-Chloro-2-hydroxyphenyl)-2-oxo-6-(trifluoromethyl)-1H-quinolin-3-yl]-(4-methoxyphenyl)acetamide mp 172–175° C.; IR (KBr, cm⁻¹) 1076, 1120, 1169, 1249, 1322, 1659, 2100–3200; ¹H NMR (300 MHz, DMSO-d₆)δ 3.42 (2H, m), 3.72 (3H, s), 6.75 (2H, d, J=8.7 Hz), 6.91 (2H, d, J=8.6 Hz), 6.96 (1H, d, J=8.7 Hz), 7.02 (1H, d, J=2,6 Hz), 7.24 (1H, s), 7.34 (1H, dd, J=8.7 and 2.6 Hz), 7.54 (1H, d, J=8.6 Hz), 7.82 (1H, dd, J=8.7 and 1.7 Hz), 9.30 (1H, brd s), 9.91 (1H, brd s), 12.44 (1H, brd s); MS m/e 503 (MH⁺).

EXAMPLE 33

N-[4-(5-Chloro-2-hydroxyphenyl)-2-oxo-6-(trifluoromethyl)-1H-quinolin-3-yl]-(4-hydroxyphenyl)acetamide mp 218–221° C.; IR (KBr, cm⁻¹) 1120,1170,1323,1661, 2800–3300; ¹H NMR (300 MHz, DMSO-d₆)δ 3.4 (2H, m), 6.58 (2H, d, J=8.4 Hz), 6.77 (2H, d, J=8.4 Hz), 6.97 (1H, d, J=8.7 Hz), 7.06 (1H, d, J=2.6 Hz), 7.25 (1H, s), 7.34 (1H, dd, J=8.7 and 2.6 Hz), 7.54 (1H, d, J=8.6 Hz), 7.82 (1H, d, J=8.7 Hz), 9.17 (1H, s), 9.25 (1H, s), 9.92 (1H, s), 12.44 (1H, s); MS m/e 487 (M-H)⁻.

EXAMPLE 34

3-Amino-4-(5-chloro-2-methoxyphenyl)-8-(trifluoromethyl)quinolin-2(1H)-one mp 265–266° C.; IR (KBr, cm⁻¹) 1670,1300,1126; ¹H NMR (300 MHz, CDCl₃)δ 7.57 (1H, d, J=7.8 Hz), 7.49 (1H, d, J=7.8 Hz), 7.39–7.35 (dd, 1H, J=2.7 Hz and J=9.0 Hz), 7.27(1H, t, J=7.2 Hz), 7.11(s, 1H), 6.94 (d, 1H, J=8.7 Hz); MS m/e 368 (MH⁺).

Anal. calcd. for $C_{17}H_{12}ClF_3N_2O_2$: C, 55.37;H, 3.28; N, 7.60. Found: C, 55.40;H, 3.43; N, 7.50.

EXAMPLE 35

3-Amino-4-(5-chloro-2-hydroxyphenyl)-5-(trifluoromethyl)quinolin-2(1H)-one mp 267–268° C.; IR (KBr, cm⁻¹) 1666,1338,1136; ¹H NMR (300 MHz, DMSO-d₆)δ 7.59 (1H, d, J=7.9 Hz), 7.50 (1H, d, J=6.8 Hz), 7.35–7.30 (m, 1H), 7.25 (1H, dd, J=2.6 and 8.7 Hz), 6.97 (s, 1H), 6.92 (d, 1H, J=8.7 Hz); MS m/e 354 (MH⁺).

Anal. calcd. for $C_{16}H_{10}ClF_3N_2O_2$: C, 51.51;H; 3.21; N, 7.51. Found: C, 51.88;H, 2.72; N, 7.48.

EXAMPLE 36

3-Amino-4-(5-chloro-2-hydroxyphenyl)-5,7-bis(trifluoromethyl)quinolin-2(1H)-one mp 230–233° C.; IR (KBr, cm⁻¹) 1674, 1278, 1134; ¹H NMR (300 MHz, DMSO-d₆)δ 7.88 (1H, s), 7.67 (1H, s), 7.29–7.25 (m, 1H), 7.03 (1H, s), 6.97 (s, 1H), 6.92 (d, 1H, J=8.7 Hz); MS m/e 422 (MH⁺).

Anal. calcd. for $C_{17}H_9ClF_6N_2O_2$: C, 48.30;H, 2.15; N, 6.63. Found: C, 48.54;H, 2.57; N, 6.11.

EXAMPLE 37

3-Amino-4-(5-chloro-2-methoxyphenyl)-5,7-bis-(trifluoromethyl)quinolin-2(1H)-one mp 265–267° C.; IR (KBr, cm⁻¹) 1670,1278,1130; MS m/e 436 (MH⁺).

EXAMPLE 38

3-Amino-4-(5-chloro-2-methoxyphenyl)-6-chloro-(trifluoromethyl)quinolin-2(1H)-one mp>300° C.; IR (KBr, cm⁻¹ ) 3368,1658,1246; ¹H NMR (300 MHz, CDCl₃)δ 7.47–7.43 (1H, dd, J=2.7 and 9.0 Hz), 7.23–7.19 (2H, dd, J=2.7 and 9.0 Hz), 7.13 (d, 1H, J=8.4 Hz), 7.04 (1H, d, J=8.7 Hz), 6.89 (d, 1H, J=2.1 Hz); MS m/e 334 (MH⁺).

Anal. calcd. for $C_{16}H_{12}Cl_2N_2O_2$:C, 57.33;H, 3.61; N, 8.36. Found: C, 57.22;H, 3.79; N, 8.22.

EXAMPLE 39

3-Amino-4-(5-chloro-2-hydroxyphenyl)-6-chloroquinolin-2(1H)-one mp 184–185° C.; IR (KBr, cm⁻¹) 3500–2700,1652,1250; ¹H NMR (300 MHz, DMSO-d₆)δ 7.34 (1H, dd, J=8.7 and 2.7 Hz), 7.26 (1H, d, J=8.4 Hz), 7.19 (1H, dd, J=8.7 and 2.4 Hz), 7.13 (1H, d, J=2.7 Hz), 7.04 (1H, d, J=8.7 Hz), 6.65 (1H, d, J=2.4 Hz); MS m/e 320 (MH⁺).

Anal. calcd. for $C_{15}H_1°Cl_2N_2O_2.0.5H_2O$: C, 54.52;H, 3.33; N, 8.48. Found: C, 54.92;H, 3.44; N, 8.29.

EXAMPLE 40

3-Amino-4-(5-chloro-2-methoxyphenyl)-6,7-dichloroquinolin-2(1H)-one mp>300° C.; IR (KBr, cm⁻¹) 1672,1248; ¹H NMR (300 MHz, CDCl₃)δ 7.55–7.51 (1H, dd, J=2.7 and 9.0 Hz), 7.43 (1H, s), 7.25 (d, 1H, J=9.0 Hz), 7.22 (1H, d, J=2.7 Hz), 6.71 (1H, s); MS m/e 368 (MH⁺).

Anal. calcd. for $C_{16}H_{11}Cl_3N_2O_2$:C, 51.99;H, 3.00; N, 7.58. Found: C, 52.15;H, 3.20; N, 7.59.

EXAMPLE 41

3-Amino-4-(5-chloro-2-hydroxyphenyl)-6,7-dichloroquinolin-2(1H)-one mp 305–307° C.; IR (KBr, cm⁻¹) 3300,1668,1264; ¹H NMR (300 MHz, DMSO-d₆)δ 7.35 (1H, s), 7.22 (1H, s), 7.12 (1H, d, J=2.7 Hz), 7.06 (1H, t, J=2.7 Hz), 6.97 (1H, s); MS m/e 354 (MH⁺).

Anal. calcd. for $C_{15}H_9Cl_3N_2O_2$: C, 50.66;H, 2.55; N, 7.88. Found: C, 50.82;H, 2.51; N, 7.63.

EXAMPLE 42

3-Amino-4-(5-chloro-2-methoxyphenyl)-6-chloro-7-(trifluoromethyl)quinolin-2(1H)-one mp 252–253° C.; IR (KBr, cm⁻¹) 1672,1278,1314,1130; ¹H NMR (300 MHz, CDCl₃)δ 7.68(1H, s), 7.56–7.52 (1H, dd, J=2.7 and 8.7 Hz), 7.26 (d, 1H, J=6.9 Hz), 7.24 (1H, s), 6.74(1H, s), 3.70(3H, s); MS m/e 402 (MH⁺).

Anal. calcd. for $C_{17}H_9ClF6N_2O_2$: C, 50.64;H, 2.75; N, 6.95. Found: C, 50.59;H, 3.02; N, 6.77.

EXAMPLE 43

3-Amino-4-(5-chloro-2-hydroxyphenyl)-6-chloro-7-(trifluoromethyl)quinolin-2(1H)-one mp 245–246° C.; IR (KBr, cm⁻¹) 1314,1232,1138; ¹H NMR (300 MHz, DMSO-d₆)δ 7.68 (1H, s), 7.35 (1H, dd, J=8.7 and 2.7 Hz), 7.24 (1H, d, J=2.7 Hz), 7.16(1H, d, J=2.7 Hz), 7.04(1H, d, J=8.7 Hz), 6.81(s, 1 H); MS m/e 388 (MH⁺).

Anal. calcd. for $C_{16}H_9Cl_2F_3N_2O_2$: C, 49.38;H, 2.33; N, 7.20. Found: C, 49.49;H, 2.54; N, 6.91.

EXAMPLE 44

3-Amino-4-(5-chloro-2-hydroxyphenyl)-6-chloro-5-(trifluoromethyl)quinolin-2(1H)-one mp 139–140° C.; IR (KBr, cm⁻¹) 1668,1334,1138,1134; ¹H NMR (300 MHz, DMSO-d₆)δ 7.47–7.40 (2H, dd, J=12.0 Hz), 7.23 (1H, d, J=6.6 Hz), 6.95 (1H, d, J=8.7 Hz), 6.85 (1H, s); MS m/e 388 (MH⁺).

Anal. calcd. for $C_{16}H_9Cl_2F_3N_2O_2$: C, 49.38;H, 2.33; N, 7.20. Found: C, 49.65;H, 2.76; N, 6.58.

EXAMPLE 45

3-Amino-4-(5-chloro-2-methoxyphenyl)-6-chloro-5-(trifluoromethyl)quinolin-2(1H)-one mp 228° C.; ¹H NMR (300 MHz, DMSO)δ 7.44–7.39 (3H, m), 7.14 (1H, d, J=8.7 Hz), 6.91 (d, 1H, J=2.7 Hz), 3.77(3H, s); MS m/e 402 (MH⁺).

Anal. calcd. for $C_{17}H_{11}Cl_2F_3N_2O_2$: C, 50.64;H, 2.75; N, 6.95. Found: C, 51.00;H, 2.92; N, 6.82.

EXAMPLE 46

3-Amino-4-(5-chloro-2-hydroxyphenyl)-6-iodoquinolin-2(1H)-one mp 160–162° C.; IR (KBr, cm$^{-1}$) 1656,1276; $^1$H NMR (300 MHz, DMSO)δ 7.46–7.43 (1H, dd, J=1.8 and 8.4 Hz), 7.36–7.32 (1H, dd, J=2.7 and 8.7 Hz), 7.12 (d, 1H, J=2.7 Hz), 7.08–7.02(3H, m), 6.98 (d, 1H, J=1.8 Hz); MS m/e 412 (MH$^+$).

Anal. calcd. for $C_{15}H_{10}ClN_2O_2$: C, 43.66;H, 2.44; N, 6.79. Found: C, 43.93;H, 2.55; N, 6.54.

EXAMPLE 47

4-(5-Chloro-2-methoxyphenyl)-3-[(4-methoxyphenyl)amino]-6-trifluoromethyl)quinolin-2(1H)-one mp 245–246° C.; $^1$H NMR (300 MHz, DMSO)δ 7.59–7.46 (3H, m), 7.21–7.18 (1H, dd, J=2.7 and 8.7 Hz), 7.02 (s, 1H), 6.95(d, J=2.7 Hz, 1 H), 6.86 (1H, d, J=8.7 Hz), 6.53–6.49(4H, m), 3.64 (3H, s), 3.62(s, 3H); MS m/e 474 (MH$^+$).

EXAMPLE 48

4-(5-Chloro-2-hydroxyphenyl)-3-[(4-hydroxyphenyl)amino]-6-(trifluoromethyl)quinolin-2(1H)-one mp 145–165° C.; $^1$H NMR (300 MHz, CD$_3$OD)δ 7.51–7.42 (2H, m), 7.28 (1H, s), 6.99–6.95 (dd, 1H, J=2.4 and 8.7 Hz), 6.82(d, 1H, J=2.4 Hz), 6.68–6.59 (3H, m), 6.42–6.25(2H, m); MS m/e 446 (MH$^+$).

Anal. calcd. for $C_{22}H_{14}ClF_3N_2O_3 \cdot 0.5H_2O$: C, 57.92;H, 3.29; N, 6.14. Found: C, 57.56;H, 3.39; N, 6.06.

EXAMPLE 49

4-(5-Chloro-2-hydroxyphenyl)-3-[(3.5-dihydroxyphenyl)-amino]-6-(trifluoromethyl)quinolin-2(1H)-one mp 148–160° C.; $^1$H NMR (300 MHz, CD$_3$OD)δ 7.58–7.48 (2H, dd, J=8.4 and 2.7 Hz), 7.41 (1H, s), 7.08–7.04 (dd, 1H, J=2.7 and 8.7 Hz), (d, 1H, J=2.7 Hz), 6.80 (1H, d, J=8.7 Hz), 5.77(2H, s), 5.73(s, 1H) ; MS m/e 462 (MH$^+$).

EXAMPLE 50

4-(5-Chloro-2-methoxyphenyl)-3-[(3.5-dimethoxyphenyl)-amino]-6-(trifluoromethyl)quinolin-2(1H)-one mp 253–254° C.; $^1$H NMR (300 MHz, CD$_3$OD)δ 7.84 (1H, d, J=2.7 Hz), 7.60 (1H, d, J=2.4 Hz), 7.44–7.40 (m, 2H), 7.00 (1H, d, J=8.4 Hz), 7.02 (d, 1H, J=8.7 Hz), 6.54 (2H, s), 6.41 (t, 1H, J=2.4 Hz), 3.74(s, 6H), 3.64(s, 3H); MS m/e 548 (MH$^+$).

EXAMPLE 51

4-(5-Chloro-2-methoxyphenyl)-3-[(3.5-di hydroxyphenyl)-amino]-6-(trifluoromethyl)quinolin-2(1H)-one mp 155–165° C.; $^1$H NMR (300 MHz, CD$_3$OD)δ 7.58–7.45 (2H, dd, J=8.4 and 3.0 Hz), 7.27 (1H, s), 7.21 (d, 1H, J=2.7 Hz), 7.0 (1H, s), 6.94 (d, 1H, J=9.0 Hz), 5.73(2H, s), 3.76(s, 6H) ; MS m/e 476 (MH$^+$).

Anal. calcd. for $C_{23}H_{16}ClF_3N_2O_4$: C, 56.81;H, 3.50; N, 5.76. Found: C, 56.49;H, 3.58; N, 5.36.

EXAMPLE 52

4-(5-Chloro-2-methoxyphenyl)-3-[(4-hydroxyphenyl)amino]-6-(trifluoromethyl)quinolin-2(1H)-one mp 165–175° C.; $^1$H NMR (300 MHz, CD$_3$OD)δ 7.51–7.42 (2H, dd, J=2.1 and 7.6 Hz), 7.14 (2H, m), 6.94(s, 1H), 6.75 (d, 1H, J=8.7 Hz), 6.62(d, 2H, J=8.1 Hz), 6.39 (2H, d, J=8.4 Hz), 3.75 (3H, s); MS m/e 460 (MH$^+$).

Anal. calcd. for $C_{23}H_{16}ClF_3N_2O_3$: C, 58.74;H, 3.62; N, 5.96. Found: C, 58.09;H, 3.68; N, 5.61.

| Ex. No. | Compound | MP °C. | Empirical Formula | Elemental Analysis Calc'd. | Found |
|---|---|---|---|---|---|
| 53 | N-[4-(5-Chloro-2-hydroxyphenyl)-2-oxo-6-(trifluoromethyl)-1H-quinolin-3-yl]-4-(trifluoromethyl)benzenesulfonamide | 215–225 (dec.) | $C_{23}H_{13}ClF_6N_2O_4S \cdot 0.1H_2O$ | C, 45.55 H, 2.60 N, 4.82 | C, 47.40 H, 2.57 N, 4.64 |
| 54 | N-[4-(5-Chloro-2-hydroxyphenyl)-1-methyl-2-oxo-6-(trifluoro-methyl)-1H-quinolin-3-yl]-4-nitrobenzenesulfonamide | 220–235 (dec.) | $C_{23}H_{15}ClF_3N_3O_6S$ | HRMS* 554.0400 (MH$^+$) | HRMS* 554.0388 (MH$^+$) |
| 55 | 3-Amino-4-(2-hydroxyphenyl)-6-(trfluoromethyl)quinolin-2(1H)-one | 244–245 | $C_{16}H_{11}F_3N_2O_2 \cdot 0.25H_2O$ | C, 59.15 H, 3.39 N, 8.63 | C, 59.32 H, 3.38 N, 8.56 |
| 56 | 4-(2-Methoxyphenyl)-3-phenyl-amino-6-(trifluoromethyl)quinolin-2(1H)-one | 241–243 | $C_{23}H_{17}F_3N_2O_2$ | C, 67.31 H, 4.18 N, 6.83 | C, 67.54 H, 4.19 N, 6.63 |
| 57 | 3-Amino-4-(2-hydroxyphenyl)-1-methyl-6-(tnfluoromethyl)quinolin-2(1 H)-one | 215–216 | $C_{17}H_{13}F_3N_2O_2 \cdot 0.25H_2O$ | C, 60.21 H, 3.98 N, 8.26 | C, 60.00 H, 3.65 N, 8.01 |
| 58 | 3-Aminp-4-(2-methoxy-5-nitro-phenyl)-6-(trifluoromethyl)quinolin-2(1 H)-one | 273–274 | $C_{17}H_{12}F_3N_3O_4 \cdot 0.33 C_4H_8O_2$ | C, 53.88 H, 3.62 | C, 53.49 H, 3.59 |

-continued

| Ex. No. | Compound | MP °C. | Empirical Formula | Elemental Analysis Calc'd. | Found |
|---|---|---|---|---|---|
| | | | | N 10.28 | N, 9.99 |
| 59 | 3-Amino-4-(4-hydroxyphenyl)-6-(trifluoromethyl)quinolin-2(1 H)-one | 241–243 | $C_{16}H_{11}F_3N_2O_2.0.25H_2O$ | C, 59.17 H, 3.57 | C, 59.29 H, 3.46 |
| | | | | N, 8.63 | N, 8.23 |
| 60 | 3-Amino-4-(5-bromo-2-hydroxy-phenyl)-6-(trifluoromethyl)quinolin-2(1H)-one | 246–247 | $C_{16}H_{10}BrF_3N_2O_2.0.1$ $C_6H_{12}$ | C, 48.89 H, 2.82 | C, 49.25 H, 2.87 |
| | | | | N, 6.87 | N, 6.97 |
| 61 | 3-Amino-4-(3-chloro-4-methoxy-phenyl)-6-(trifluoromethyl)quinolin-2(1H)-one | 248–249 | $C_{17}H_{12}ClF_3N_2O_2.0.66H_2O$ | C, 53.62 H, 3.53 | C, 53.30 H, 3.46 |
| | | | | N, 7.36 | N, 7.41 |
| 62 | 3-Amino-4-(3-methoxyphenyl)-6-(trifluoromethyl)quinolin-2(1H)-one | 166–167 | $C_{17}H_{13}F_3N_2O_2.0.17H_2O$ | C, 60.53 H, 3.98 | C, 60.52 H, 3.92 |
| | | | | N, 8.31 | N, 8.11 |
| 63 | 3-Amino-4-(3-hydroxyphenyl)-6-(trifluoromethyl)quinolin-2(1H)-one | >360 | $C_{16}H_{11}F_3N_2O_2.0.2CH_2Cl_2$ | C, 57.69 H, 3.41 | C, 57.78 H, 3.27 |
| | | | | N, 8.31 | N, 8.04 |
| 64 | N-[4-(5-Chloro-2-hydroxyphenyl)-2-oxo-6-(trifluoromethyl)-1H-quinolin-3-yl]-4-nitrobenzene-sulfonamide. | 286–287 (dec.) | $C_{22}H_{13}ClF_3N_3O_6S$ | HRMS* 540.0244 $(MH^+)$ | HRMS* 540.0237 $(MH^{30})$ |
| 65 | N-[4-(5-Chloro-2-methoxyphenyl)-2-oxo-6-(trifluoromethyl)-1H-quinolin-3-yl]-4-fluorobenzene-sulfonamide | 154–156 | $C_{23}H_{15}ClF_4N_2O_4S$ | C, 52.42 H, 2.87 | C, 52.29 H, 2.90 |
| | | | | N, 5.32 | N, 5.19 |
| 66 | N-[4-(5-Chloro-2-hydroxyphenyl)-2-oxo-6-(trifluoromethyl)-1 H-quinolin-3-yl]-(4-fluorobenzene)sulfonamide | 265–268 (dec.) | $C_{22}H_{13}ClF_4N_2O_4S.0.33$ $H_2O$ | C, 50.93 H, 2.65 | C, 50.93 H, 2.80 |
| | | | | N, 5.40 | N, 5.18 |
| 67 | N-[4-(5-Chloro-2-hydroxyphenyl)-2-oxo-6-(trifluoromethyl)-1H-quinolin-3-yl]naphthalene-2-sulfonamide | 291–293 (dec.) | $C_{26}H_{16}ClF_3N_2O_4S.0.66$ $H_2O$ | C, 5606 H, 3.14 | C, 56.12 H, 3.39 |
| | | | | N, 5.03 | N, 4.77 |
| 68 | 3-Amino-4-(5-chloro-2-hydroxy-phenyl)-1-methyl-6-(trifluoro-methyl)quinolin-2(1H)-one | 167–168 | $C_{17}H_{12}ClF_3N_2O_2$ | C, 58.02 H, 3.25 | C, 57.79 H, 3.30 |
| | | | | N, 3.01 | N, 4.84 |
| 69 | 3-Amino-4-(2-hydroxy-5-nitro-phenyl)-6-(trifluoromethyl)quinolin-2(1H)-one | 215 (dec.) | $C_{16}H_{10}F_3N_3O_4.0.5H_2O$ .0.12$C_6H_6$ | C, 52.38 H, 3.08 | C, 52.36 H, 2.95 |
| | | | | N, 10.93 | N, 10.43 |
| 70 | 3-Amino-4-(5-chloro-2-methoxy-phenyl)-1-methyl-6-(trifluoro-methyl)quinolin-2(1H)-one | 216–217 | $C_{18}H_{14}ClF_3N_2O_2.0.5H_2O$ | C, 55.18 H, 3.86 | C, 55.25 H, 3.54 |
| | | | | N, 7.15 | N, 6.77 |
| 71 | 3-Amino-4-(3-chloro-4-hydroxy-phenyl)-6-(trifluoromethyl)quinolin-2(1H)-one | 277 (dec.) | $C_{16}H_{10}ClF_3N_2O_2.0.1$ $CH_2Cl_2$ | C, 54.18 H, 2.84 | C, 53.80 H, 2.98 |
| | | | | N, 7.90 | N, 7.60 |

*HRMS [32 [0 High Resolution Mass Spectrometry

EXAMPLE 72

4-(5-Chloro-2-methoxyphenyl)-3-(methylamino)-6-(trifluoromethyl)quinolin-2(1H)-one Step A. 4-(5-Chloro-2-methoxyphenyl)-3-[[(1H-benzotriazol-1-yl)methyl]amino]-6-(trifluoromethyl)quinolin-2(1H)-one A solution of 3-amino-4-(5-chloro-2-methoxyphenyl)-6-(trifluoromethyl)quinolin-2(1H)-one(500 mg, 1.36 mmol), benzotriazole methanol (202.9 mg, 1.36 mmol) and absolute ethanol (5 mL) was heated to 60° C. overnight (18 hours). The resulting suspension was then cooled and the solids were collected. The solids were then washed with ethanol and air dried affording 4-(5-chloro-2-methoxyphenyl)-3-[[(1H-benzotriazol-1-yl)methyl]amino]-6-(trifluoromethyl)quinolin-2(1H)-one (487 mg, 71.6%).

mp 217–219° C. $^1$H NMR (DMSO-$d_6$)δ 12.45(bs, 1H), 7.96(d,1H, J=8.28 Hz), 7.78(d, 1H, J=8.32 Hz), 7.57(dd,1H, J=8.68, 1.71 Hz), 7.51 (m, 2H), 6.51(m, 1H), 6.06(dd, 1H, J=14.02, 8.63 Hz), 5.93(dd, 1H, J=14.04, 8.63 Hz), 3.26(s, 3H). MS m/e: 499 (M-H)$^-$.

Step B. 4-(5-Chloro-2-methoxyphenyl)-3-(methylamino)-6-(trifluoromethyl)quinolin-2(1H)-one Sodium borohydride(151.2 mg, 4.0 mmol) was added to a solution of 4-(5-chloro-2-methoxyphenyl)-3-[[(1H-benzotriazol-1-yl)methyl]amino]-6-(trifluoromethyl)quinolin-2(1H)-one (1.0 g, 2.0 mmol) in absolute ethanol and heated to reflux for thirty minutes. The reaction was cooled, acidified with 10% citric acid, extracted with ethyl acetate, dried over magnesium sulfate, and concentrated. The resulting solid was then chromatographed on silica gel affording 4-(5-chloro-2-hydroxyphenyl)-3-(methylamino)-6-(trifluoromethyl)quinolin-2(1H)-one (200 mg, 26.1%).

mp 238–240° C. $^1$H NMR (DMSO-$d_6$)δ 12.36(bs, 1H), 7.54(dd, 1H, J=8.85, 2.79 Hz), 7.44(m, 2H), 7.31 (d, 1H, J=2.80 Hz), 7.22(d, 1H, J=8.96 Hz), 6.86(m, 1H), 6.06(m, 1H), 3.72(s, 3H), 2.27(d, 3H, J=5.51 Hz). MS m/e: 382 (MH$^+$).

Anal. calcd. for $C_{18}H_{14}N_2O_2F_3Cl$: C,56.48;H,3.69; N,7.21. Found: C,56.46;H,3.77; N,7.21.

EXAMPLE 73

4-(5-Chloro-2-hydroxyphenyl)-3-(methylamino)-6-(trifluoromethyl)quinolin-2(1H)-one Sodium hydride (1.3 g, 27.9 mmol) was added to a solution of 3-amino-4-(5-chloro-2-hydroxyphenyl)-6-(trifluoromethyl)quinolin-2(1H)-one (4.7 g, 13.3 mmol) and dry DMF at ambient temperature under nitrogen. Neat chloromethyl methyl ether was added and the reaction was stirred overnight. The reaction was then diluted with saturated ammonium chloride and extracted with ethyl acetate. The organic layer was dried over magnesium sulfate and concentrated. Chromatography on silica gel was used to isolated a mixture of O,N- and O,O-bis methoxymethyl quinolones (3.24 g) from remaining starting material. The bis methoxymethyl mixture was dissolved in dry DMF and sodium hydride(375.4 mg, 8 mmol) was added at ambient temperature under nitrogen. Dimethyl sulfate(0.76 ml, 8.0 mmol) was added and the reaction was stirred for 1 hour. The reaction mixture was then diluted with saturated ammonium chloride and extracted with ethyl acetate. The organic layer was dried over magnesium sulfate and concentrated. The crude material was taken up in dry methylene chloride and boron tribromide(1 M in methylene chloride, 2.1 eq) was added at ambient temperature under nitrogen. After 6 hours, the reaction mixture was quenched with saturated sodium bicarbonate and extracted with methylene chloride. The organic layer was combined, dried over magnesium sulfate, and concentrated. Chromatography on silica gel afforded 4-(5-chloro-2-hydroxyphenyl)-3-(methylamino)-6-(trifluoromethyl)quinolin-2(1H)-one (1.03 g, 21%).

mp 260–262° C. $^1$H NMR (DMSO-d$_6$)δ 12.33(bs, 1H), 9.77(bs, 1H), 7.40(m, 3H), 7.20(m, 1H), 6.98(m, 2H), 6.03 (m, 1H), 2.32(m, 3H). MS m/e: 368 (M-H)$^-$.

Anal. calcd. for C$_{17}$H$_{12}$ClF$_3$N$_2$O$_2$.0.O$_2$H$_2$O: C, 54.84;H, 3.35; N, 7.52. Found: C, 54.84;H, 3.42; N, 7.24.

EXAMPLE 74

4-(5-Chloro-2-methoxyphenyl)-3-[(4-pyridylmethyl) amino]-6-(trifluoromethyl)quinolin-2(1H)-one mp 205–208° C. $^1$H NMR (DMSO-d$_6$)δ 12.47(bs, 1H), 8.35(d, 2H, J=5.51 Hz), 7.44(m, 3H), 7.03(d, 1H, J=8.95 Hz), 6.95(d, 1H, J=2.70 Hz), 6.81(d, 2H, J=5.75 Hz), 6.75(bs, 1H), 6.62(t, 1H, J=7.48 Hz), 4.01 (d, 2H, J=7.43 Hz), 3.46(s, 3H). MS: 459 (M-H)$^-$.

EXAMPLE 75

4-(5-Chloro-2-methoxyphenyl)-3-[(phenylmethyl) amino]-6-(trifluoromethyl)quinolin-2(1H)-one mp 218–220° C. $^1$H NMR (DMSO-d$_6$)δ 12.45(bs, 1H), 7.47(m, 3H), 7.23(m, 3H), 7.11(d, 1H, J=8.93 Hz), 7.03(d, 1H, J=2.68 Hz), 6.89(d, 2H, J=6.88 Hz), 6.81 (bs,1H), 6.26(t,1H, J=7.01 Hz), 3.90(d, 2H, J=7.00 Hz), 3.53(s, 3H). MS m/e: 458 (MH$^+$).

EXAMPLE 76

4-(5-Chloro-2-methoxyphenyl)-3-[(2-furanylmethyl) amino]-6-(trifluoromethyl)quinolin-2(1H)-one mp 198–200° C. $^1$H NMR (DMSO-d$_6$)δ 12.45(bs, 1H), 7.52(m, 4H), 7.25(m, 2H), 7.22(m, 2H), 6.88(m, 1H), 6.22 (m, 1H), 5.77(t, 2H, J=6.35 Hz), 3.66(m, 5H). MS m/e: 448 (MH$^+$).

EXAMPLE 77

4-(5-Chloro-2-methoxyphenyl)-3-[(2-imidazolylmethyl)amino]-6-(trifluoromethyl) quinolin-2(1H)-one mp 155–159° C. $^1$H NMR (DMSO-d$_6$)δ 12.49(bs, 1H), 7.54(m, 3H), 7.25(m, 2H), 6.89(m, 3H), 6.23(m, 1H), 3.78(t, 2H, J=4.83 Hz), 3.70(s, 3H). MS m/e: 448 (MH$^+$).

EXAMPLE 78

4-(5-Chloro-2-methoxyphenyl)-3-[(3-thienylmethyl) amino]-6-(trifluoromethyl)quinolin-2(1H)-one mp 188–190° C. $^1$H NMR (DMSO-d$_6$)δ 12.45(bs, 1H), 7.50(m, 4H), 7.18(d, 1H, J=8.95 Hz), 7.12(d, 1H, J=2.70 Hz), 6.97(m, 1H), 6.85(bs, 1H), 6.72(dd,1H, J=4.96, 1.27 Hz), 6.05(t,1H, J=6.69 Hz), 3.84(d, 2H, J=6.55 Hz), 3.62(s, 3H). MS m/e: 464 (M+).

EXAMPLE 79

4-(5-Chloro-2-methoxyphenyl)-3-[(1-methyl pyrrolylmethyl)amino]-6-(trifluoromethyl)quinolin-2 (1H)-one mp 121–124° C. $^1$H NMR (DMSO-d$_6$)δ 12.50(bs, 1H), 7.71(m, 1H), 7.56(m, 3H), 7.25(m, 2H), 6.92(bs,1H), 6.63 (m, 1H), 5.84(m, 1H), 5.76(m, 1H), 5.37(t, 1H, J=5.72 Hz), 4.14(m, 1H), 3.72(s, 3H), 3.30(s, 3H). MS m/e: 461 (M-H)$^-$.

EXAMPLE 80

4-(5-Chloro-2-methoxyphenyl)-3-[[(4-fluoro phenyl) methyl]amino]-6-(trifluoromethyl)quinolin-2(1H)-one mp 232–234° C. $^1$H NMR (DMSO-d$_6$)δ 12.45(bs, 1H), 7.47(m, 3H), 7.10(d, 1H, J=8.95 Hz), 7.02(m, 3H), 6.88(m, 2H), 6.78(m, 1H), 6.38(t, 1H, J=7.07 Hz), 3.91 (d, 2H, J=6.93 Hz), 3.54(s, 3H). MS m/e: 476 (MH$^+$).

EXAMPLE 81

4-(5-Chloro-2-methoxyphenyl)-3-[(3-pyridylmethyl) amino]-6-(trifluoromethyl)quinolin-2(1H)-one mp 160–163° C. $^1$H NMR (DMSO-d$_6$)δ 12.48(bs,1H), 8.34(dd, 1H, J=4.56, 1.78 Hz), 8.00(d, 1H, J=1.53 Hz), 7.46(m, 1H), 7.24(m, 2H), 7.03(m, 2H), 6.66(bs,1H), 6.51 (t,1H, J=7.25 Hz), 4.0(m, 2H), 3.50(s, 3H). MS m/e: 459 (MH$^+$).

EXAMPLE 82

4-(5-Chloro-2-methoxyphenyl)-3-[(2-furanylmethyl) amino]-6-(trifluoromethyl)quinolin-2(1H)-one mp 193–196° C. $^1$H NMR (DMSO-d$_6$)δ 12.47(bs, 1H), 7.54(m, 2H), 7.47(m, 2H), 7.21(d, 1H, J=8.97 Hz), 7.14(d, 1H, J=2.68 Hz), 6.31(m, 1H), 5.98(d, 1H, J=3.17 Hz), 5.91(t, 1H, J=6.68 Hz), 3.84(m, 2H), 3.65(s, 3H). MS m/e: 448 (MH$^+$).

EXAMPLE 83

4-(5-Chloro-2-methoxyphenyl)-3-[[(2-furanyl)-2-propenyl]amino]-6-(trifluoromethyl)quinolin-2(1H)-one mp 191–193° C. $^1$H NMR (DMSO-d$_6$)δ 12.45(bs,1H), 7.54(m, 5H), 7.27(d, 1H, J=2.69 Hz), 7.21 (d,1H, J=8.95 Hz), 6.86(bs,1H), 6.42(dd, 1H, J=3.28, 1.84 Hz), 6.31 (d, 1H, J=3.31 Hz), 6.03(m, 2H), 5.74(m, 1H), 3.62(s, 3H). MS m/e: 474 (M-H)$^-$.

EXAMPLE 84

4-(5-Chloro-2-methoxyphenyl)-3-[[[4-(thiomethyl) phenyl]-methyl]amino]-6-(trifluoromethyl)quinolin-2(1H)-one mp 95–97° C. $^1$H NMR (DMSO-d$_6$)δ 12.45(bs, 1H), 7.47(m, 3H), 7.10(m, 3H), 7.02(d, 1H, J=2.68 Hz), 6.81(m, 3H), 6.30(t, 1H, J=7.04 Hz), 3.87 (m, 2H), 3.53(s, 3H), 2.41 (s, 3H). MS m/e: 504 (M-H)$^-$.

EXAMPLE 85

4-(5-Chloro-2-methoxyphenyl)-3-[(cyclohexylmethyl)amino]-6-(trifluoromethyl) quinolin-2(1H)-one mp 208–210° C. $^1$H NMR (DMSO-d$_6$)δ 12.43(bs, 1H), 7.56(dd, 1H, J=8.84, 2.72 Hz), 7.48(m, 2H), 7.30(d,1H, J=2.69 Hz), 7.25(d, 1H, J=8.97 Hz), 5.85(t,1H, J=7.09 Hz), 3.71 (s, 3H), 2.38(m, 1H), 1.59(m, 4H), 1.12(m, 6H). MS m/e: 464 (MH+).

EXAMPLE 86

4-(5-Chloro-2-methoxyphenyl)-3-[[[4-(methoxy)phenyl]-methyl]amino]-6-(trifluoromethyl)quinolin-2(1H)-one mp 175–178° C. $^1$H NMR (DMSO-$d_6$)δ 12.45(bs, 1H), 7.51(m, 2H), 7.42(d, 1H, J=8.39 Hz), 7.15(d, 1H, J=8.96 Hz), 7.07(d, 1H, J=2.69 Hz), 6.82(m, 5H), 6.09(t, 1H, J=6.70 Hz), 3.80(m, 2H), 3.69(s, 3H), 3.58(s, 3H). MS m/e: 488 (MH+).

Anal. calcd. for $C_{25}H_{20}N_2O_2F_2Cl$: C, 61.42;H, 4.14; N, 5.39. Found: C, 61.21;H, 4.14; N, 5.39.

What is claimed is:

1. A compound of the formula

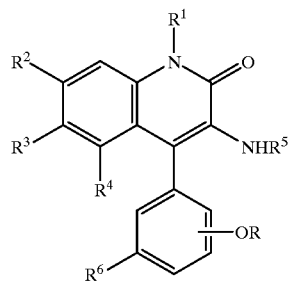

I wherein

R and $R^1$ each are independently hydrogen or methyl; $R^2$, $R^3$ and $R^4$ each are independently hydrogen, halogen, nitro or trifluoromethyl provided $R^2$, $R^3$ and $R^4$ are not all hydrogen;

$R^5$ is hydrogen, $C_{1-4}$alkyl, $C_{1-4}$alkylsulfonyl, trifluoromethylsulfonyl, naphthylsulfonyl, $C_{1-4}$alkylcarbonyl, diphenylphosphinyl, cyclohexylmethyl, pyridylmethyl, furanylmethyl, furanyl-2-propenyl, imidazolylmethyl, thienylmethyl, 1-methyl pyrrolylmethyl, unsubstituted or substituted phenyl, phenylmethyl, phenylsulfonyl, phenylcarbonyl, phenylalkylcarbonyl or phenylglyoxyloyl wherein said phenyl substituent is selected from the group consisting of one or two fluoro, hydroxy, trifluoromethyl, amino, methoxy, methylthio and nitro; and $R^6$ is bromo, chloro or nitro;

or a nontoxic pharmaceutically acceptable salt thereof.

2. A compound of claim 1 having the formula

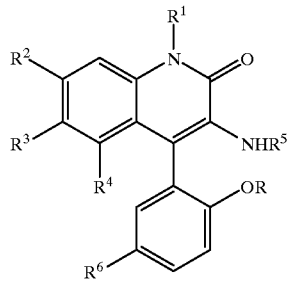

II wherein

R and $R^1$ each are independently hydrogen or methyl; $R^2$, $R^3$ and $R^4$ each are independently hydrogen, chloro, nitro or trifluoromethyl provided $R^2$, $R^3$ and $R^4$ are not all hydrogen;

$R^5$ is hydrogen, $C_{1-4}$ alkyl, $C_{1-4}$ alkylsulfonyl, trifluoromethylsulfonyl, cyclohexylmethyl, pyridylmethyl, furanylmethyl, furanyl-2-propenyl, imidazolylmethyl, thienylmethyl, 1-methyl pyrrolylmethyl, unsubstituted or substituted phenyl, phenylmethyl, phenylcarbonyl or phenylsulfonyl wherein said phenyl substituent is selected from one or two fluoro, hydroxy, trifluoromethyl, methoxy, methylthio and nitro; and $R^6$ is chloro;

or a nontoxic pharmaceutically acceptable salt thereof.

3. A compound of claim 2 having the formula

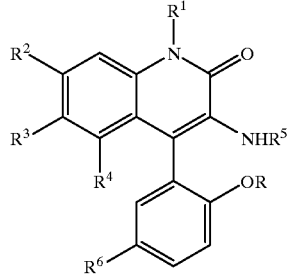

II wherein

R is hydrogen;

$R^1$ is hydrogen or methyl; $R^2$, $R^3$ and $R^4$ each are independently chloro, nitro or trifluoromethyl;

$R^5$ is hydrogen, methyl, $C_{14}$ alkylsulfonyl, trifluoromethylsulfonyl, unsubstituted or substituted phenyl, phenylmethyl, phenylmethyl, phenylcarbonyl or phenylsulfonyl wherein said phenyl substituent is selected from one or two fluoro, hydroxy, trifluoromethyl, methoxy, methylthio and nitro; and $R^6$ is chloro;

or a nontoxic pharmaceutically acceptable salt thereof.

4. A compound of claim 1 selected from the group consisting of:

3-Amino-4-(5-chloro-2-hydroxyphenyl)-6-(trifluoromethyl) quinolin-2(1H)-one;

3-Amino-4-(5-chloro-2-hydroxyphenyl)-7-(trifluoromethyl) quinolin-2(1H)-one;

4-(5-Chloro-2-hydroxyphenyl)-3-(methylamino)-6-(trifluoromethyl) quinolin-2(1H)-one;

N-[4-(5-Chloro-2-hydroxyphenyl)-2-oxo-6-(trifluoromethyl)-1H-quinolin-3-yl]trifluoromethanesulfonamide;
N-[4-(5-Chloro-2-hydroxyphenyl)-2-oxo-7-(trifluoromethyl)-1H-quinolin-3-yl]trifluoromethanesulfonamide;
N-[4-(5-Chloro-2-hydroxyphenyl)-2-oxo-6-(trifluoromethyl)-1H-quinolin-3-yl]methanesulfonamide;
N-[4-(5-Chloro-2-hydroxyphenyl)-2-oxo-6-(trifluoromethyl)-1H-quinolin-3-yl]phenylsulfonamide;
3-Amino-4-(5-chloro-2-hydroxyphenyl)-5,7-dichloroquinolin-2(1H)-one;
N-[4-(5-Chloro-2-hydroxyphenyl)-2-oxo-6-(trifluoromethyl)-1H-quinolin-3-yl]aminocarboxylic acid, phenylmethyl ester;
3-Amino-4-(5-chloro-2-hydroxyphenyl)-6-nitroquinolin-2(1H)-one;
3-Amino-4-(5-chloro-2-hydroxyphenyl)-7-nitroquinolin-2(1H)-one;
N-[4-(5-Chloro-2-hydroxyphenyl)-2-oxo-6-(trifluoromethyl)-1H-quinolin-3-yl]diphenylphosphinamid;
3-Amino-4-(5-chloro-2-hydroxyphenyl)-5,6-dichloroquinolin-2(1H)-one;
N-[4-(5-Chloro-2-hydroxyphenyl)-2-oxo-6-(trifluoromethyl)-1H-quinolin-3-yl]-4-hydroxybenzenesulfonamide;
3-Amino-4-(5-chloro-2-hydroxyphenyl)-5-(trifluoromethyl)quinolin-2(1H)-one;
3-Amino-4-(5-chloro-2-hydroxyphenyl)-5,7-bis(trifluoromethyl)quinolin-2(1H)-one;
3-Amino-4-(5-chloro-2-hydroxyphenyl)-6-chloroquinolin-2(1H)-one;
3-Amino-4-(5-chloro-2-hydroxyphenyl)-6-chloro-7-(trifluoromethyl) quinolin-2(1H)-one;
3-Amino-4-(5-chloro-2-hydroxyphenyl)-6-chloro-5-(trifluoromethyl) quinolin-2(1H)-one;
3-Amino-4-(5-chloro-2-hydroxyphenyl)-6-iodoquinolin-2(1H)-one;
4-(5-Chloro-2-hydroxyphenyl)-3-[(4-hydroxyphenyl)amino]-6-(trifluoromethyl)quinolin-2(1H)-one;
4-(5-Chloro-2-hydroxyphenyl)-3-[(3,5-dihydroxyphenyl)amino]-6-(trifluoromethyl)quinolin-2(1H)-one;
4-(5-Chloro-2-methoxyphenyl)-3-[(3,5-dihydroxyphenyl)amino]-6-(trifluoromethyl)quinolin-2(1H)-one;
4-(5-Chloro-2-methoxyphenyl)-3-[(4-hydroxyphenyl)amino]-6-(trifluoromethyl)quinolin-2(1H)-one;
N-[4-(5-Chloro-2-hydroxyphenyl)-2-oxo-6-(trifluoromethyl)-1H-quinolin-3-yl]-4-(trifluoromethyl)benzenesulfonamide;
N-[4-(5-Chloro-2-hydroxyphenyl)-1-methyl-2-oxo-6-(trifluoro-methyl)-1H-quinolin-3-yl]-4-nitrobenzenesulfonamide;
3-Amino-4-(4-hydroxyphenyl)-6-(trifluoromethyl)quinolin-2(1H)-one;
3-Amino-4-(5-bromo-2-hydroxy-phenyl)-6-(trifluoromethyl)quinolin-2(1H)-one;
N-[4-(5-Chloro-2-hydroxyphenyl)-2-oxo-6-(trifluoromethyl)-1H-quinolin-3-yl]-4-nitrobenzenesulfonamide;
N-[4-(5-Chloro-2-hydroxyphenyl)-2-oxo-6-(trifluoromethyl)-1H-quinolin-3-yl]-(4-fluorobenzene)sulfonamide;
3-Amino-4-(5-chloro-2-hydroxy-phenyl)-1-methyl-6-(trifluoro-methyl) quinolin-2(1H)-one;
3-Amino-4-(2-hydroxy-5-nitro-phenyl)-6-(trifluoromethyl) quinolin-2(1H)-one; and
3-Amino-4-(3-chloro-4-hydroxy-phenyl)-6-(trifluoromethyl)quinolin-2(1H)-one.

5. A compound of claim 4 selected from the group consisting of:
3-Amino-4-(5-chloro-2-hydroxyphenyl)-6-(trifluoromethyl)quinolin-2(1H)-one;
4-(5-Chloro-2-hydroxyphenyl)-3-(methylamino)-6-(trifluoromethyl) quinolin-2(1H)-one;
N-[4-(5-Chloro-2-hydroxyphenyl)-2-oxo-6-(trifluoromethyl)-1H-quinolin-3-yl]trifluoromethanesulfonamide;
N-[4-(5-Chloro-2-hydroxyphenyl)-2-oxo-7-(trifluoromethyl)-1H-quinolin-3-yl]trifluoromethanesulfonamide;
N-[4-(5-Chloro-2-hydroxyphenyl)-2-oxo-6-(trifluoromethyl)-1H-quinolin-3-yl]phenylsulfonamide;
3-Amino-4-(5-chloro-2-hydroxyphenyl)-5,6-dichloroquinolin-2(1H)-one;
3-Amino-4-(5-chloro-2-hydroxyphenyl)-5-(trifluoromethyl)quinolin-2(1H)-one;
3-Amino-4-(5-chloro-2-hydroxyphenyl)-5,7-bis(trifluoromethyl)quinolin-2(1H)-one;
4-(5-Chloro-2-hydroxyphenyl)-3-[(4-hydroxyphenyl)amino]-6-(trifluoromethyl)quinolin-2(1H)-one;
4-(5-Chloro-2-hydroxyphenyl)-3-[(3,5-dihydroxyphenyl)amino]-6-(trifluoromethyl)quinolin-2(1H)-one;
4-(5-Chloro-2-methoxyphenyl)-3-[(3,5-dihydroxyphenyl)amino]-6-(trifluoromethyl)quinolin-2(1H)-one;
N-[4-(5-Chloro-2-hydroxyphenyl)-2-oxo-6-(trifluoromethyl)-1H-quinolin-3-yl]-4-(trifluoromethyl)benzenesulfonamide;
N-[4-(5-Chloro-2-hydroxyphenyl)-1-methyl-2-oxo-6-(trifluoro-methyl)-1H-quinolin-3-yl]-4-nitrobenzenesulfonamide;
N-[4-(5-Chloro-2-hydroxyphenyl)-2-oxo-6-(trifluoromethyl)-1H-quinolin-3-yl]-4-nitrobenzenesulfonamide; and
N-[4-(5-Chloro-2-hydroxyphenyl)-2-oxo-6-(trifluoromethyl)-1H-quinolin-3-yl]-(4-fluorobenzene)sulfonamide.

6. A pharmaceutical composition for the treatment of disorders responsive to openers of the large conductance calcium-activated potassium channels comprising a therapeutically effective amount of a compound as defined in claim 1 in association with a pharmaceutically acceptable carrier or diluent.

7. A method for the treatment of disorders responsive to opening of the large conductance calcium-activated potassium channels in a mammal in need thereof, which comprises administering to said mammal a therapeutically effective amount of a compound as defined in claim 1.

8. A method of claim 7 wherein said disorder is ischemia, stroke, convulsions, epilepsy, asthma, irritable bowel syndrome, migraine, traumatic brain injury, spinal cord injury, male erectile dysfunction and urinary incontinence.

9. The method of claim 8 wherein the disorder is stroke.

* * * * *